United States Patent
Bryan et al.

(10) Patent No.: US 11,708,926 B2
(45) Date of Patent: Jul. 25, 2023

(54) CONNECTOR FOR FORMING A FLUID FLOW PATHWAY

(71) Applicant: OVERX MEDICAL LIMITED, Tring (GB)

(72) Inventors: Matthew Robert Bryan, Tring (GB); Alistair Richard Ian Wilson, Tring (GB); Andrew Honour, Amersham (GB)

(73) Assignee: OVERX MEDICAL LIMITED, Tring (GB)

( * ) Notice: Subject to any disclaimer, the term of this patent is extended or adjusted under 35 U.S.C. 154(b) by 0 days.

(21) Appl. No.: 17/778,797

(22) PCT Filed: Nov. 19, 2020

(86) PCT No.: PCT/EP2020/082757
§ 371 (c)(1),
(2) Date: May 20, 2022

(87) PCT Pub. No.: WO2021/099508
PCT Pub. Date: May 27, 2021

(65) Prior Publication Data
US 2022/0412495 A1 Dec. 29, 2022

(30) Foreign Application Priority Data

Nov. 22, 2019 (GB) .................................... 1917030

(51) Int. Cl.
*F16L 37/32* (2006.01)
*F16L 37/098* (2006.01)
*A61M 39/10* (2006.01)
*A61M 39/26* (2006.01)
*F16L 37/40* (2006.01)

(52) U.S. Cl.
CPC .......... *F16L 37/32* (2013.01); *A61M 39/1011* (2013.01); *F16L 37/098* (2013.01);
(Continued)

(58) Field of Classification Search
CPC ............ A61M 39/26; A61M 2039/267; A61M 2039/268; A61M 39/10; A61M 39/1011;
(Continued)

(56) References Cited

U.S. PATENT DOCUMENTS 3,838,843 A * 10/1974 Bernhard ......... A61B 5/150389
285/14
6,964,406 B2 * 11/2005 Doyle ...................... F16L 29/04
251/149.6
(Continued)

FOREIGN PATENT DOCUMENTS

| WO | WO 2004/082756 A1 | 9/2004 |
| WO | WO 2006/037638 A1 | 4/2006 |
| WO | WO 2016/210300 A1 | 12/2016 |

OTHER PUBLICATIONS

International Search Report and Written Opinion for International Application No. PCT/EP2020/082757, dated Mar. 3, 2021.

*Primary Examiner* — David Colon-Morales
(74) *Attorney, Agent, or Firm* — Wolf, Greenfield & Sacks, P.C.

(57) ABSTRACT

A connector for forming a fluid flow pathway by connection with a reciprocal connector. Both the connector and reciprocal connector include a fluid flow blockage part sheathed within an axially compressible sheath part. A first bearing surface receives an urging force to retract the blockage part axially along the sheath part. A terminal end of the sheath part defines a second bearing surface containing a fluid flow opening with the fluid flow blockage part retractably therein. A first chassis part includes a first catch part. A second chassis part includes a second catch part and a third bearing surface spaced from the second catch part along the second chassis part. Retraction of the blockage part forms a fluid flow pathway not sooner than immediately when the open- (Continued)

ings meet to allow fluid transfer the openings avoiding fluid leakage between connected connectors.

20 Claims, 20 Drawing Sheets

(52) U.S. Cl.
CPC . *A61M 2039/267* (2013.01); *A61M 2039/268* (2013.01); *F16L 37/40* (2013.01)

(58) Field of Classification Search
CPC ........... A61M 2039/1027; F16L 37/098; F16L 37/10; F16L 29/04; F16L 37/40; F16L 37/32; A61J 1/2051; A61J 1/2089
See application file for complete search history.

(56) References Cited

U.S. PATENT DOCUMENTS

| | | | | |
|---|---|---|---|---|
| 7,044,441 B2* | 5/2006 | Doyle | .................. | A61M 39/26 251/149.6 |
| 7,118,560 B2* | 10/2006 | Bonaldo | ................ | A61M 39/26 604/537 |
| 7,396,051 B2* | 7/2008 | Baldwin | ................ | A61M 39/26 604/905 |
| 7,645,274 B2* | 1/2010 | Whitley | ................ | A61M 39/26 604/537 |
| 9,861,805 B2* | 1/2018 | Dennis | .................. | A61M 39/26 |
| 9,931,497 B2* | 4/2018 | Lopez | .................. | A61M 39/10 |
| 9,933,094 B2* | 4/2018 | Fangrow | ............... | A61M 39/18 |
| 10,016,586 B2* | 7/2018 | Lopez | .................. | A61M 39/10 |
| 10,105,529 B2* | 10/2018 | Ryan | .................. | A61M 39/1011 |
| 10,478,606 B2* | 11/2019 | Yang | .................... | A61M 39/24 |
| 10,806,666 B2* | 10/2020 | Chih | .................... | A61J 1/2096 |
| 11,207,514 B2* | 12/2021 | Kakinoki | .............. | A61M 39/10 |
| 2004/0124389 A1* | 7/2004 | Phillips | ................. | A61M 39/26 604/905 |
| 2015/0258324 A1* | 9/2015 | Chida | .................. | A61M 39/10 604/538 |
| 2018/0140819 A1 | 5/2018 | Yang | | |

* cited by examiner

CONNECTOR FOR FORMING A FLUID FLOW PATHWAY

CROSS-REFERENCE TO RELATED APPLICATIONS

This application is a national stage filing under 35 U.S.C. § 371 of International Patent Application Serial No. PCT/EP2020/082757, filed Nov. 19, 2020, which claims priority to GB application 1917030.7, filed Nov. 22, 2019. The contents of these applications are incorporated herein by reference in their entireties.

FIELD

The invention relates to connectors for safely forming a fluid-tight connection between fluid flow conduits to form a fluid flow pathway therebetween.

BACKGROUND

When connecting and disconnecting two fluid flow conduits in fluid communication, to form (or break) a fluid flow pathway between them, it may be critically important that no leakage of fluid takes place during the process of connection/disconnection. This may be because, for example, the fluid being communicated is highly toxic or dangerous to human health. This may often occur in medical settings in which fluid pathways may convey toxic (e.g. cytotoxic) fluids for use in medical treatment of patients (e.g. cancer treatment).

Clinicians tasked with preparing and applying such treatments to patients are regularly required to connect a particular treatment fluid vessel, vial or bag containing a treatment fluid, to another fluid vessel, vial or bag (or to a patient intravenously), via an intermediate fluid flow conduit connecting the two in fluid communication. The quality of this connection, and the integrity of the fluid flow it provides, is safety critical.

Leakages occurring during the process of creating (or terminating) such connections as necessary in the regular duties of a clinician, are potentially hazardous and dangerous. They are often avoided by great care being applied by clinicians when making/breaking such fluid flow conduit connections, but mistakes and accidents happen.

The invention aims to address this problem and to provide a connector apparatus for use in creating (or terminating) connections between fluid flow conduits to safely form (or terminate) fluid flow pathways.

SUMMARY

In a first aspect, the invention provides a connector adapted for forming a fluid flow pathway therethrough by connection with a reciprocal connector, wherein both the connector and the reciprocal connector each comprise a fluid flow blockage part sheathed within an axially compressible sheath part and comprising a first bearing surface configured for receiving an urging force to push the blockage part to retract axially along the sheath part and a terminal end of the sheath part defines a second bearing surface containing a fluid flow opening with the fluid flow blockage part retractably therein. A first chassis part comprises a first catch part. A second chassis part comprises a second catch part and a third bearing surface spaced from the second catch part along the second chassis part. The axial distance (Y) between the second bearing surface and the first catch part exceeds the axial distance (X) between the second bearing surface and the second catch part. The axial distance (L) between the third bearing surface and the second catch part exceeds the axial distance (H) between the first bearing surface and the first catch part. Consequently, the connector may be connectable to the reciprocal connector with respective fluid flow openings mutually aligned such that $X+L \geq H+Y$ whereby said retraction takes place not before said mutually aligned respective fluid flow openings meet to form a fluid flow pathway between the connector and the reciprocal connector. This ensures that a fluid flow pathway is formed, by retracting respective fluid flow blockage parts from the aligned fluid flow openings after, or not sooner than immediately when, the openings meet to allow fluid transfer directly from one opening to the other opening in a safe manner avoiding fluid leakage, or spillage between connected such connectors. Of course, the inner bore of the sheath of each connector may be in fluid communication with a suitable fluid flow output port of the connector to which any desired onward/inward fluid flow transfer conduit may be connected to permit fluid flow from or to the inner bore of the sheath. Similarly, the above arrangements ensure that a fluid flow pathway is closed, by reversing the aforementioned retraction of respective fluid flow blockage parts from the aligned fluid flow openings before, or not later than immediately when, the openings separate to terminate fluid transfer from one opening to the other opening in a safe manner avoiding fluid leakage, or spillage when disconnecting such connectors.

Desirably, before the second catch part of the connector engages the first catch part of the reciprocal connector, the sheath part of the connector and the sheath part of the reciprocal connector are reciprocally compressed at respective second bearing surfaces thereat to form a compression interface surrounding said respective fluid flow openings, whereby said retraction takes place not before said compression interface is formed. In this way, a greater degree of security may be achieved at the interface where (surrounding) the two fluid flow openings after they meet.

Desirably, before the second catch part of the connector engages the first catch part of the reciprocal connector, the fluid flow blockage part of the connector is retracted axially by a said urging force applied at the first bearing surface thereof by a said third bearing surface of the reciprocal connector, and the fluid flow blockage part of the reciprocal connector is retracted axially by a said urging force applied at the first bearing surface thereof by a said third bearing surface of the connector, whereby said retraction takes place not before said compression interface is formed. In this way, a secure interface surrounding the meeting of the two fluid flow openings is achieved while the two connectors are being pushed together to cause the retraction of the fluid flow blockage part before full connection (of the catch parts) is achieved. This allows one to implement a desired degree of retraction needed to open (un-block) the fluid flow opening fully before respective catches 'catch' to hold the connected connectors together in that condition/state, until disconnected.

It is to be understood that the process of safe connection described herein applies equally in reverse order to allow safe disconnection of two connected connectors according to any aspect of the invention.

Preferably, the compression interface surrounding said respective fluid flow openings forms a sealing interface fully surrounding the respective fluid flow openings securing fluid communication therebetween.

Desirably, the fluid flow blockage part comprises a fluid flow conduit part including a fluid flow conduit opening configured to enter into fluid communication with said sheath part when said retraction takes place, thereby to form a part of said fluid flow pathway.

Preferably, the axial retraction of a said fluid flow conduit part moves that fluid flow conduit part along a said sheath part from a closed state of fluid isolation from said fluid flow opening thereof, to an open state of fluid communication with the fluid flow opening thereof.

Desirably, a surface of the sheath part is shaped to abut a conduit opening of the fluid flow conduit part when in said closed state, and to be spaced from the conduit opening of the fluid flow conduit part when in said open state.

Preferably, the sheath part is resiliently deformable.

Desirably, the first chassis part comprises a first resilient biasing member upon which the first catch part is disposed, wherein the connector is connectable to the reciprocal connector to flex the first resilient biasing member to urge the first catch part of the connector towards the second catch part of the reciprocal connector.

Preferably, the second chassis part comprises a second resilient biasing member upon which the second catch part is disposed, wherein the connector is connectable to the reciprocal connector to flex the second resilient biasing member to urge the second catch part of the connector towards the first catch part of the reciprocal connector.

Desirably, one of the first catch part and the second catch part comprises a latch and the other of the first catch part and the second latch part comprises a detent configured to receive and retain the latch.

Preferably, the first catch part comprises the latch and the second catch part comprises the detent.

The connector may comprise an indexing mechanism configured for positioning the counter piece by rotation through a predefined interval of rotation.

The indexing mechanism may comprise a cylindrical cam and a reciprocating cam follower, wherein the cam follower is connected to the fluid flow conduit part and is engaged within a cam slot of the cylindrical cam such that said axial retraction of the fluid flow blockage (e.g. conduit) part causes the cam follower to urge rotation of the cylindrical cam around the axis of the fluid flow conduit part.

In a second aspect, the invention provides a pair of connectors in which each connector of the pair of connectors comprises a connector according to the connector described above, whereby one connector of said pair of connectors is said reciprocal connector.

In a third aspect, the invention provides a connector system comprising a first connector and a second connector, wherein both the first connector and the second connector are adapted to connect to each other, wherein the first connector and the second connector each comprises a respective fluid flow blockage part sheathed within an axially compressible respective sheath part. A terminal end of each respective sheath part defines a terminal bearing surface containing a fluid flow opening with the fluid flow blockage part retractably therein. The first connector comprises a first chassis part comprising a first catch part and a first bearing surface spaced from the first catch part along the first chassis part. The second connector comprises a second catch part and a second bearing surface configured for receiving an urging force to push the fluid flow blockage part of the second connector to retract axially along the respective sheath part. The axial distance (Y) between the second catch part and the terminal bearing surface of the second connector exceeds the axial distance (X) between the terminal bearing surface of the first connector and the first catch part. The axial distance (L) between the first bearing surface and the first catch part exceeds the axial distance (H) between the second bearing surface and the second catch part. The first connector is connectable to the second connector with respective fluid flow openings mutually aligned such that before the first catch part of the first connector engages the second catch part of the second connector. The condition $X+L \geq H+Y$ exists such that the retraction takes place not before said mutually aligned respective fluid flow openings meet to form a fluid flow pathway between the first connector and the second connector.

In the connector system, the first connector may be connectable to the second connector such that the sheath part of the first connector and the sheath part of the second connector are reciprocally compressed at respective terminal bearing surfaces thereat to form a compression interface surrounding said respective fluid flow openings, whereby said retraction takes place not before said compression interface is formed.

Desirably, the fluid flow blockage part comprises a fluid flow conduit part including a fluid flow conduit opening configured to enter into fluid communication with said sheath part when said retraction takes place, thereby to form a part of said fluid flow pathway.

In the connector system, the first connector may be connectable to the second connector such that the fluid flow conduit part of the second connector is retracted axially by a said urging force applied at the second bearing surface by said first bearing surface whereby said retraction takes place not before said compression interface is formed.

Desirably, in the connector system the compression interface surrounding said respective fluid flow openings forms a sealing interface fully surrounding the respective fluid flow openings securing fluid communication therebetween.

Preferably, in the connector system the axial retraction of a said fluid flow conduit part moves that fluid flow conduit part along a said sheath part from a closed state of fluid isolation from said fluid flow opening thereof, to an open state of fluid communication with the fluid flow opening thereof.

In the connector system, desirably, a surface of a said sheath part is shaped to abut a conduit opening of the fluid flow conduit part when in said closed state, and to be spaced from the conduit opening of the respective fluid flow conduit part when in said open state.

In the connector system one or each said sheath part may be resiliently deformable.

Preferably, according to the connector system, the first chassis part comprises a first resilient biasing member upon which the first catch part is disposed, wherein the first connector is connectable to the second connector to flex the first resilient biasing member to urge the first catch part of the connector towards the second catch part of the second connector.

Desirably, one of the first catch part and the second catch part of the connector system comprises a latch and the other of the first catch part and the second latch part comprises a detent configured to receive and retain the latch.

The first catch part of the connector system may comprise the latch and the second catch part may comprise the detent.

In the connector system, one or each of the first and second connectors may comprise an indexing mechanism configured for positioning the counter/counting piece by rotation through a predefined interval of rotation.

The indexing mechanism may comprise a cylindrical cam and a reciprocating cam follower, wherein the cam follower is connected to the fluid flow conduit part and is engaged within a cam slot of the cylindrical cam such that said axial retraction of the fluid flow conduit part causes the cam follower to urge rotation of the cylindrical cam around the axis of the fluid flow blockage (or conduit) part.

In relation to the indexing mechanism referred to above in relation to any aspect of the invention, the cylindrical cam may comprise the counting piece whereby said rotation of the cylindrical cam results in a corresponding rotation of the counting piece.

Preferably, the cylindrical cam is configured such that each time a connection is made by the connector, the cylindrical cam advances in rotation by an amount sufficient to bring a successive one or a succession of counting (e.g. numerical) symbols into alignment for viewing through a viewing window formed in the connector. This allows a user to visually determine how many times the connector has been used to form such a connection.

The cam slot may comprise one or more cam channels (e.g. a zigzag channel) within which a respective said cam follower moveably resides. The cylindrical cam may be moveable relative to the cam follower and/or the cam follower may be moveable relative to the cylindrical cam to cause the cylindrical cam to rotate about its cylindrical axis. The cylindrical cam may comprise two separate cam channels comprising a first cylindrical cam channel and a second cylindrical cam channel. The indexing mechanism may comprise a first reciprocating cam follower residing within the first cam channel, and a second reciprocating cam follower residing within the second cam channel, wherein each of the first and second cam followers is connected to the fluid flow conduit part and is engaged within a respective cam slot of the cylindrical cam such that said axial retraction of the fluid flow conduit part causes each of the first and second cam followers to urge rotation of the cylindrical cam around the axis of the fluid flow conduit part.

The cylindrical cam, or one/both of the first cylindrical cam and the second cylindrical cam may comprise a circumferential, or semi-circumferential, channel within an inner, concave cylindrical wall of a cylindrical cam ring.

An end of the cam slot(s) may terminate at a respective terminal notch configured to receive (and preferably also to retain) a respective cam follower to prevent further rotation of the cylindrical cam. A terminal notch, or notches, may be shaped and configured to prevent any axial movement of the cam follower in a direction parallel to the axis along which the fluid flow blockage part is retractable. This may serve to retain the fluid flow blockage part in the fully un-retracted state preventing fluid flow through the connector. In this condition, a terminal/final counting symbol of the sequence of counting symbols may be aligned in register with the viewing window. The terminal notch ensures that the connector cannot subsequently be connected to another such connector on more than a predetermined number of occasions. This may be particularly important for safety reasons whereby the connector is deemed to require servicing, cleaning or may be considered to be unfit for further use after this number of uses. In this way, the connector is automatically rendered "safe".

Desirably, the cam slot is configured such that the cam follower can move only in one circumferential direction along the cam slot towards the terminal notch. This ensures that the indexing mechanism may count only in one order (ascent or descent) through the counting (e.g. numerical) symbols. Preferably, the cam slot comprises two opposing arrays of successive cam peaks and troughs wherein each peak of one array opposes a respective trough between two neighbouring successive peaks of the opposing array. Preferably, each such peak is circumferentially offset from the respective trough it opposes. Preferably, amongst a given of opposing trough and peak pairing, the trough of the pairing is circumferentially closer to the terminal notch than is the peak of that pairing. This may bias the circumferential direction of relative movement of the cam follower along the cam slot towards the terminal notch.

DESCRIPTION OF EMBODIMENTS

Figure 1:
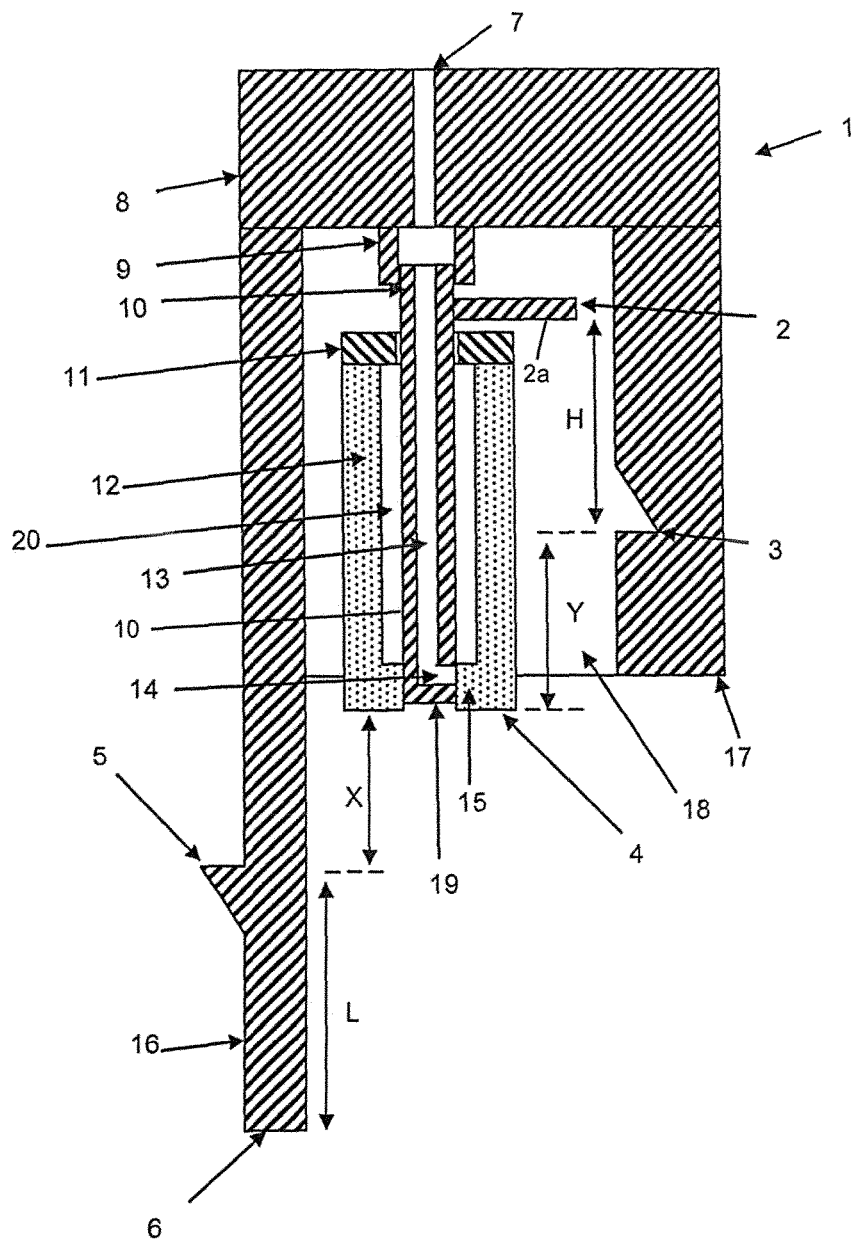
FIG. 1 shows a cross-sectional schematic view of a connector according to an embodiment of the invention.

In the drawings like items are assigned like reference symbols.

Figure 2:
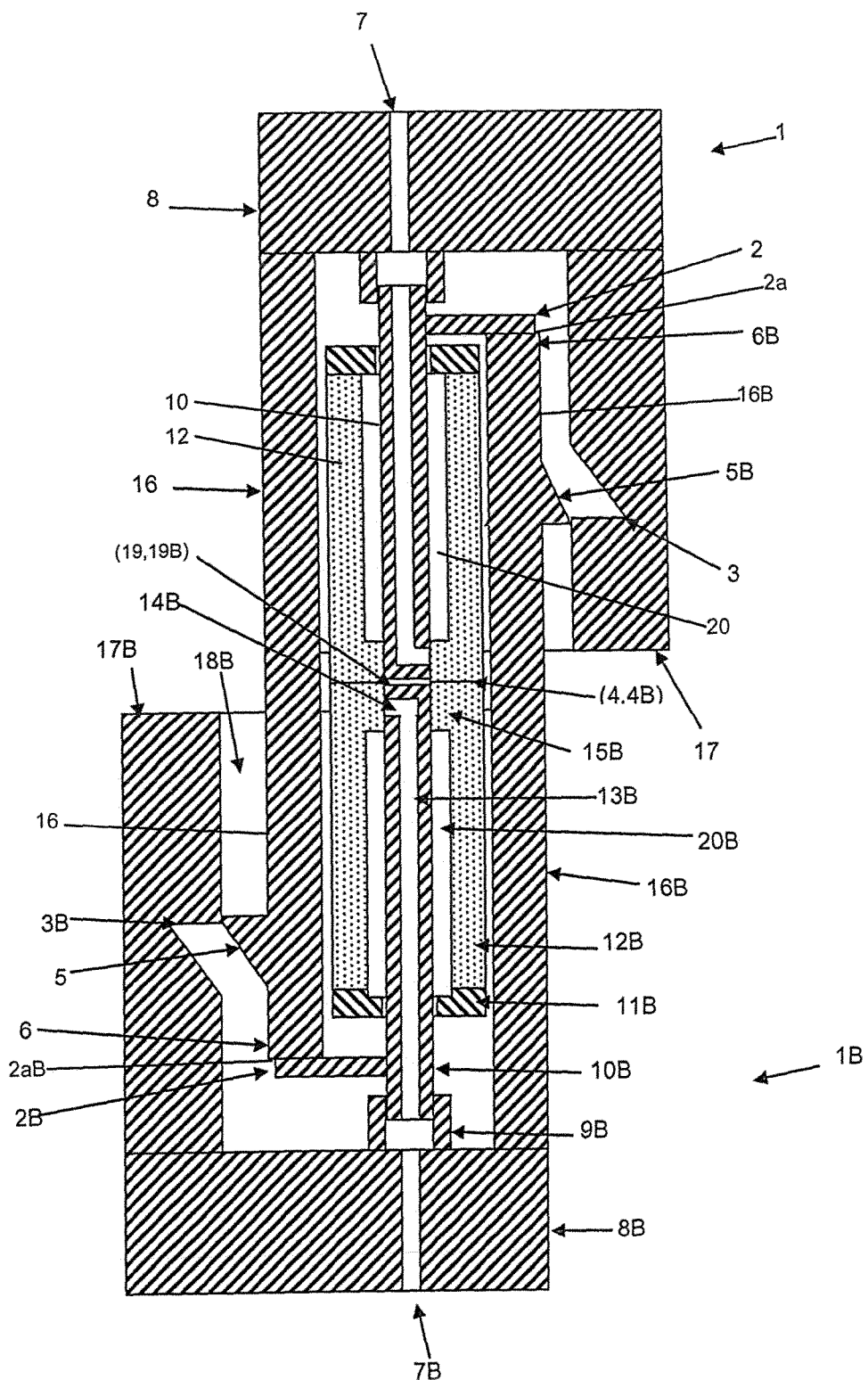
FIG. 2 shows a cross-sectional schematic view of two connectors, each identical to the connector of FIG. 1, in the process of being connected (or disconnected) according to an embodiment of the invention.

Referring to FIG. 1, there is shown a schematic cross-sectional diagram of a connector (1) according to an embodiment of the invention which is adapted for forming a fluid flow pathway by connection with a reciprocal connector. Both the connector and the reciprocal connector (1B; FIG. 2) share substantially identical features described below and arranged in such a way that the two may be connected together to form a fluid flow pathway. Put another way, two identical copies of the connector (1) may be connected together in this way, whereby any one connector is the reciprocal connector to the other.

The connector comprises a connector chassis including a chassis base portion (8) from one side of which projects a cylindrical first chassis part (17) defining a cylindrical chassis wall surrounding, and defining, a cylindrically-shaped chassis cavity (18) or void circumscribed by the cylindrical chassis wall. At a terminal end of the cylindrical chassis wall, opposite to the end at which the chassis wall (17) meets the chassis base (8), there is defined an opening permitting access to the chassis cavity (18) and permitting access to components of the connector which reside within the chassis cavity, as described in more detail below. Peripheral, terminal edges of the cylindrical chassis wall circumscribe the opening to the chassis cavity and define the perimeter of that opening. A second chassis part (16) defines an elongated and resiliently deformable limb member, or finger member, which extends from a section of the terminal edge of the cylindrical chassis wall so as to point in a direction away from the chassis cavity (18), but parallel to the longitudinal/cylindrical axis of the chassis cavity (18) and parallel to an elongated tubular flow conduit member (10) disposed within the chassis cavity, as is described in more detail below. The second chassis part terminates at a bearing surface (6) defined by the terminal end of the limb or finger member. This bearing surface is referred to hereafter as the third bearing surface, and it functions in collaboration with a first bearing surface (2a) and a second bearing surface (4) of the connector (1) and of the reciprocal connector (1B) as described in more detail below. Indeed, a first catch part (3) and a second catch part (5) act as a means to retain each one of the first, second and third bearing surfaces of the connector in a position bearing against a collaborating one of the first, second and third bearing surfaces of the reciprocal connector (16).

The first catch part (3) is formed within a surface of the cylindrical chassis wall of the first chassis part (17) and is disposed within, and faces into, the chassis cavity (18). The first catch part takes the form of a recess, notch or detent which is exposed to, and is accessible from within, the chassis cavity. Conversely the second catch part (5) is formed upon a surface of the second chassis part (16) to define a hook, anchor or claw and is disposed upon a surface of the limb member, or finger member, of the second chassis part which is opposite to the surface thereof that faces towards (or across) the opening of the connector (1). In this sense, the second catch part (5) projects in a direction radially outwardly from the longitudinal axis of the chassis cavity (18). Conversely, the recess, notch or detent defined by the first catch part faces into the chassis cavity in a direction radially inwardly towards the longitudinal axis of the chassis cavity. Of course, put another way, the radial depth of the recess, notch or detent defined by the first catch part extends into the surface of the chassis cavity wall in a direction radially outwardly from the longitudinal axis of the chassis cavity (18). In particular, the radial direction in which the radial depth of the first catch part extends into the surface of the first chassis part is diametrically opposite to the radial direction in which the radial height of the second catch part extends/projects from the surface of the second chassis part.

The shape and dimensions of the body of the second catch part at least partially reciprocate the shape and dimensions of the recess of the first catch part, such that an inserted body having a shape and dimensions corresponding to those of the second catch part, may be received by the recess of the first catch part. In this condition, the first catch part and the inserted body engage to form an interlocking connection which inhibits, obstructs or prevents removal of the inserted body from the first catch part by extraction axially. Of course, it will be understood that the inserted body in question may be the second catch part of a reciprocal connector (1B; FIG. 2) identical to the connector (1) illustrated in FIG. 1.

As mentioned above, the connector comprises an elongated tubular fluid flow conduit member (10) within and along the elongate axis of which is formed a fluid flow conduit bore (13, 14). The fluid flow conduit bore extends from a fluid flow conduit bore opening (14) and along an axially-extending direction within the fluid flow conduit (10) to a terminal fluid flow conduit distal end. The fluid flow conduit distal end is arranged in fluid communication with a fluid flow port (7) formed within the chassis base (8) of the connector, presented within the chassis cavity (18), via an intermediate flow conduit bushing (9) which is a connected to a surface of the chassis base in register with, and surrounding, an opening of the fluid flow port (7). The flow conduit bushing (9) comprises a cylindrical collar which is upstanding from the surface of the chassis base to which it is connected, and which presents an inner bushing bore within and along which the fluid flow conduit distal end (10) is slidingly (axial movement) mounted. The fluid flow conduit distal end presents an outer surface configured and shaped to reciprocate the surface shape of the inner bushing bore, and to form a fluid-tight interference fit therewith. In preferred embodiments, the flow conduit bushing is resiliently deformable to permit it to be axially compressed between the surface of the chassis base (8) to which it is attached and opposing parts of (or parts connected to) the fluid flow conduit when the fluid flow conduit is moved towards the flow conduit bushing in a direction along the axis of the bushing (and along the axis of the fluid flow conduit). In other embodiments, the flow conduit bushing (9) may be rigid. In any case, the flow conduit bushing allows a sealed fluid communication between the distal end of the fluid flow conduit (10) and the fluid flow port (7) thereby permitting fluid to flow from one to the other in either direction.

The fluid flow conduit member (10) is partially sheathed by an axially compressible elongated sheath part (12) which defines an elongated sheath cavity (20) extending along the long axis of the sheath part from a rigid sheath footing member (11), which is fixedly connected to the connector chassis within the chassis cavity (18), to a terminal fluid flow sheath opening (19) at a terminal opposite end of the sheath part. The greater part of the fluid flow conduit bore (13), but not all of it, is sheathed within the sheath part. In particular, the distal terminal end (10) of the fluid flow conduit is not sheathed within the sheath part, but is disposed within the flow conduit bushing (9) such that an intermediate portion of the fluid flow conduit extends between the fluid flow bushing and the sheath part, and resides within neither.

A first bearing member (2) is connected rigidly to the intermediate portion of the fluid flow conduit, and may be integrally formed with the intermediate portion of the fluid flow conduit. The first bearing member comprises a rigid arm which extends from an outer surface of the fluid flow conduit into the chassis cavity (18), in a direction transverse (e.g. radially, e.g. substantially perpendicular) to the longitudinal axis of the fluid flow conduit. The radial length of the rigid arm exceeds the transverse/radial dimension of the sheath part adjacent to the rigid arm, such that a surface portion of the rigid arm is visible and accessible via the chassis cavity (18) without being obscured or obstructed by the sheath part. This accessible surface portion defines a first bearing surface (2a) which will be described in more detail below.

In particular, an application of an urging force to the first bearing surface, in a direction parallel to the long axis of the fluid flow conduit (10), initiates a sliding retraction of the fluid flow conduit into the sheath cavity (20) in a direction along the longitudinal axis of the fluid flow conduit. The fluid flow conduit is configured to be slidingly movable axially within the sheath cavity in a direction along both the long axis of the sheath cavity and the long axis of the fluid flow conduit. Consequently, the fluid flow conduit is concurrently movable relative to the connector chassis, fixed sheath footing member (11) connected to the chassis and the axially compressible sheath part (12) mounted to the chassis within the chassis cavity. In particular, the sheath footing member (11) defines an annular seat against an annular surface of which a terminal end of the sheath part abuts to form a fluid-tight interface such that the sheath cavity (20) is placed in register with a central through-opening of the annular seat through which the fluid flow conduit (10) extends from within the sheath cavity (20).

The fluid flow sheath opening (19) is configured to be reversibly placed in fluid communication with the sheath cavity (18) according to the position of the fluid flow conduit within the sheath cavity and/or the fluid flow sheath opening. In particular, the sheath cavity (20) of the axially compressible sheath (12), is shaped to form a partial radial constriction (15) which ensures that the fluid flow sheath opening (19) has a bore having a diameter which is less than the diameter of the sheath cavity, but substantially matches the diameter of the proximal end of the fluid flow conduit which is arranged to be retractable insertable into the bore of the fluid flow sheath opening (19).

In particular, in the inserted (i.e. un-retracted) state, schematically illustrated in FIG. 1, the proximal end of the fluid flow conduit, containing the fluid flow conduit bore opening (14), is snugly fitted within the bore of the fluid flow sheath opening (19). This closes the fluid flow sheath opening so as to prevent fluid communication with the sheath cavity via the fluid flow sheath opening, and also so as to close the fluid flow conduit bore opening to prevent fluid communication with the fluid flow conduit bore via the fluid flow conduit bore opening (14). The transverse/radial shape and dimensions of the fluid flow conduit (i.e. transverse to the longitudinal axis thereof) reciprocally match the radial dimensions of the bore of the fluid flow sheath opening such that the former forms interference fit against the latter when inserted therein in the un-retracted state.

The fluid flow conduit bore opening (14) is a side-opening presented at a side surface of the fluid flow conduit facing towards the internal walls/bore of the axially compressible sheath (12). This side-opening (14) is pressed against, and sealed by, the bore of the fluid flow sheath opening, at the radial constriction (15), when the fluid flow conduit is in the inserted (i.e. un-retracted) state such that the radial constriction defines a sheath and seal surface. Conversely, when in the un-inserted (i.e. retracted) state in which the side-opening (14) is retracted from the constriction and not pressed against, nor sealed by, the walls/bore of the sheath cavity (20) or the bore of the fluid flow sheath opening, then the fluid flow conduit opening (14) is in fluid communication with both the fluid flow sheath opening (19) and the sheath cavity (20).

A terminal end surface (4) of the axially compressible sheath (12) is a substantially flat and annular surface extending between the perimeter of the fluid flow sheath opening (19) and the external outer diameter of the axially compressible sheath. It is against this terminal end surface that axial compression forces may be applied to the axially compressible sheath so as to compress that sheath axially. To this extent, the terminal end surface (4) of the sheath provides a second bearing surface for receiving such axial compression forces, as will be described in more detail below.

It is to be noted that the relative positions of the first bearing surface (2a), the first catch part (3), the second bearing surface (4), the second catch part (5) and the third bearing surface (6) are carefully controlled such that the following conditions are met:

Condition 1: The axial distance (Y) between the second bearing surface and the first catch part exceeds the axial distance (X) between the second bearing surface and the second catch part.

Condition 2: The axial distance (L) between the third bearing surface and the second catch part exceeds the axial distance (H) between the first bearing surface and the first catch part.

Consequently, a first connector is connectable to a reciprocal/identical second such connector with respective fluid flow sheath openings (19) mutually aligned, such that:

$$X+L \geq H+Y.$$

Consequently, these conditions ensure that the simultaneous retraction of the fluid flow conduits (10) in both the first connector and the identical second connector takes place not before mutually aligned respective fluid flow sheath openings (19) meet when a sealing interface surrounding them is formed between opposing abutted second bearing surfaces (4). This forms a secure fluid flow pathway between the first connector and the reciprocal/identical second connector.

Figure 3:
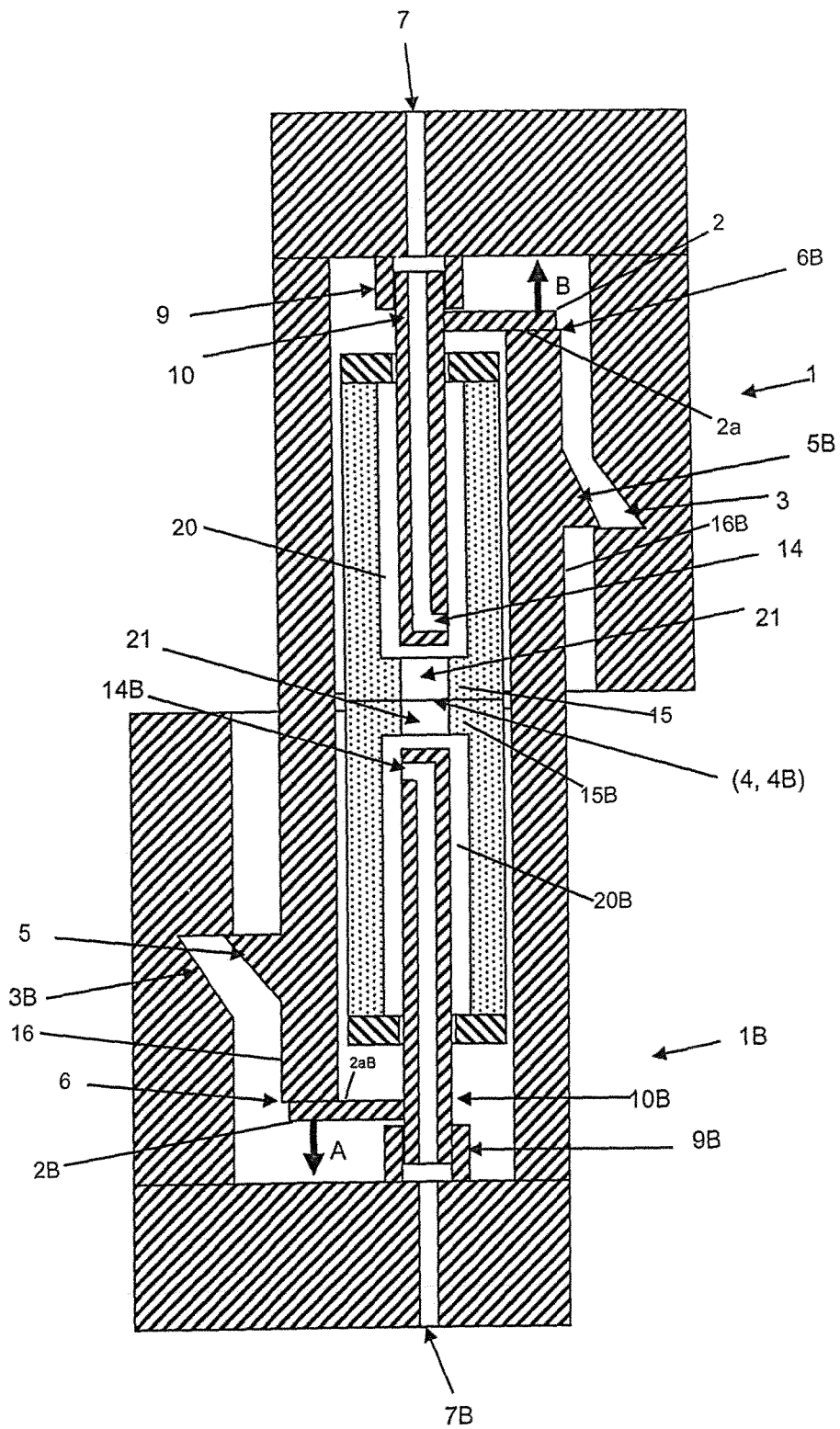
FIG. 3 shows a cross-sectional schematic view of the two connectors of FIG. 2, each identical to the connector of FIG. 1, in the connected state according to an embodiment of the invention.

FIG. 2 and FIG. 3 each schematically illustrates a cross-sectional view of such a first connector (1) and an identical/reciprocal second connector (1B) at successive stages in the process of exactly this interconnection.

As will be seen from FIGS. 2 and 3, before the second catch part (5) of the first connector (1) engages the first catch part (3B) of the reciprocal connector (1B), the sheath part (12) of the first connector (1) and the sheath part (12B) of the reciprocal connector (1B) are reciprocally compressed at respective second bearing surfaces (4, 4B) thereat to form a compression interface surrounding their respective fluid flow sheath openings (19, 19B). The retraction of the two fluid flow conduits (10, 10B) takes place not before the compression interface (4, 4B) is formed.

Similarly, before the second catch part (5) of the first connector (1) engages the first catch part (3B) of the reciprocal connector (1B), the fluid flow conduit part (10) of the first connector (1) is retracted axially by the urging force (see force vector B' of FIG. 3) applied at the first bearing surface (2a) of the rigid arm part (2) by the third bearing surface (6B) of the reciprocal connector (1B). Simultaneously, the fluid flow conduit part (10B) of the reciprocal connector (1B) is also retracted axially by an urging force (see force vector 'A' of FIG. 3) applied at the first bearing surface of the rigid arm part (2B) of the reciprocal connector (1B), by the third bearing surface (6) of the first connector (1). The simultaneous retraction of the two fluid flow conduits (10, 10B) takes place not before the compression interface (4, 4B) is formed between the two abutting second bearing surfaces of the respective two axially compressible sheaths (12, 12B) of the first connector and the reciprocal second connector.

This compression interface surrounds the respective fluid flow openings (19, 19B) of the abutting sheaths and forms a sealing interface fully surrounding the respective fluid flow openings securing fluid communication therebetween the sheath cavities (20, 20B) of the two sheaths.

The axial retraction of each fluid flow conduit part moves that respective fluid flow conduit part along the sheath part from a closed state of fluid isolation from the fluid flow opening of that sheath part (see FIG. 2), to an open state of fluid communication with that fluid flow opening thereof (see FIG. 3). The result is the formation of a secure fluid flow pathway (21) passing from one sheath cavity to the other sheath cavity (20, 20B), with each sheath cavity in fluid communication with the respective fluid flow conduit bore opening (14, 14B) of the retracted fluid flow conduit (10, 10B) within it.

As described above, in each connector (1, 1B), a surface of the bore of the fluid flow sheath opening (19, 19B) of the respective sheath part, is shaped and configured to form a sheath end seal (15, 15B) designed to abut the conduit opening (14, 14B) of the fluid flow conduit part when in the un-retracted, closed state shown in FIG. 2. However, as shown in FIG. 3, the sheath end seals (15, 15B) are spaced from the respective fluid flow conduit openings (14, 14B) when in the retracted, open state shown in FIG. 3.

The sheath parts are formed from a resiliently deformable silicone rubber in the present examples, but may be made from another resiliently deformable material as desired and appropriate.

The limb or finger formation provided by the respective second chassis part (16, 16B) of both the first connector (1) and the reciprocal second connector (1B), is a resiliently deformable member upon which the respective catch part (5, 5B) is disposed. This resilience is such as to permit the limb or finger formation (16, 16B) to flex to urge the second catch part (5) of the connector towards the first catch part (3B) of the reciprocal connector (1B), and simultaneously to urge the second catch part (5B) of the reciprocal connector (1B) towards the first catch part (3) of the first connector (1) when the limb/finger (16, 16B) of on connector is inserted into the chassis cavity (18, 18B) of the other connector to connect the two connectors, as shown in FIGS. 2 and 3. This resilient deformability/biasing action permits a 'snap-fit' of 'click-fit' of the two connectors (1, 1B) as the first and second catch parts of one connector click into place with the second and first catch parts, respectively, of the other connector as shown in FIG. 3. Subsequent radially-directed inward depression (flexure) of each limb/finger formation (16, 16B) simultaneously will disengage the first and second catch parts from each other such that application of a concurrent axial force to each connector (1, 1B) in opposite directions away from each other, allows the two connectors to fully disengage and to be separated.

It is to be understood that although not explicitly shown in FIGS. 1 to 3, in these embodiments as well as other preferred embodiments, the connector (1, 1B) also comprises a resilient biasing part (e.g. a spring—not shown) which resides in the chassis cavity (18, 18B) and is configured to bias the fluid flow conduit part (10, 10B) into the un-retracted state described above, and shown in FIG. 1 and FIG. 2. It is against this biasing force that the force vectors (see vectors 'A' and 'B' of FIG. 3) act when a given fluid flow conduit part is forced to retract. Thus, removal of these force vectors by separation of two connected connectors (1, 1B), allows the biasing force to dominate and to move the previously retracted fluid flow conduit part back into an un-retracted state. For example, a biasing part may comprise a helical spring extending in between, and urging against, opposing surfaces of the second chassis part (8, 8B) and the first bearing member (2, 2B) within the chassis cavity (18, 18B).

It will also be appreciated that the sequence of movements and interactions that occur in the act of separation of the first connector (1) and the reciprocal second connector (1B), are the reverse of the sequence of movements and interactions that occur (as described above) when the two connectors are connected together. In particular, separation of the first connector from the reciprocal second connector involves retracting the limb/finger (16, 16B) of the second chassis part of one connector from the chassis cavity (18, 18B) of the other connector, with the result that the urging force applied to the first bearing surface (2a) of the respective first bearing members of the two connectors, is withdrawn. The resilient biasing part (not shown) of each connector responds to this withdrawal of force by pushing the associated fluid flow conduit part (10, 10B) of the associated connector from the retracted state (see FIG. 3) into the un-retracted state (see FIG. 2) wherein the fluid flow conduit bore openings (14, 14B) of each connector is sealed by re-insertion into the bore of the respective fluid flow sheath opening (19, 19B) and sheath end seal (15, 15B) there. This ends fluid communication between the fluid flow conduit bores (13, 13B) of each connector. Once this re-insertion has occurred, continued separation of the two connectors separates the second bearing surface (4) of the first connector (1) from the second bearing surface (4B) of the second, reciprocal connector, such that the fluid-tight seal formed between the two surrounding the fluid flow pathway 21, is broken. However, critically, this seal is not broken until after each of the two fluid flow bore openings (14, 14B) have been sealed shut.

Thus, the first connector (1) and the reciprocal second connector (1B) may be connected and disconnected in such a way that fluid communication between the fluid flow conduits of each is only permitted after a fluid-tight seal exists between the sheaths of the two thereby allowing the formation of that fluid communication safely, and the breaking of that fluid-tight seal is only permitted after a fluid-tight seal exists which closes each fluid flow conduit bore opening thereby allowing the safe separation of the two connectors. The geometry of the connector ensures that this is done automatically by the simple action of a press-fit connection of the connectors and by the simple action of a pull-apart separation of them, as appropriate.

Figure 4:
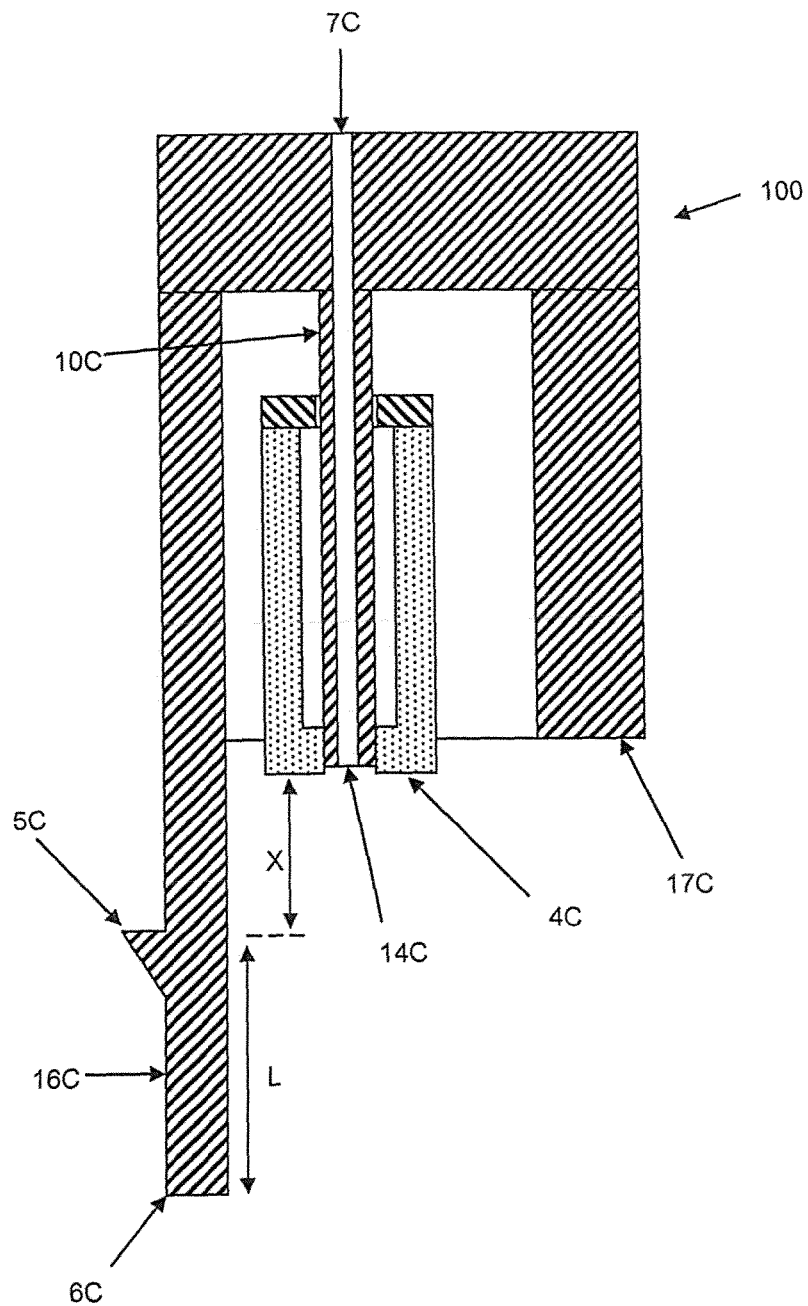
FIG. 4 shows a cross-sectional schematic view of a connector according to an embodiment of the invention.

FIG. 4 schematically illustrates a cross-section view of a connector (100) according to an embodiment of the invention, which is similar to the connector described above in the environment referred to with reference to FIG. 1, except for the following differences. In particular, the connector of FIG. 4 comprises a fluid flow conduit (10C) which is rigidly connected to the chassis base of the connector in fluid communication with the fluid flow port (7C) which passes through the chassis base. A bushing component (item 9, FIG. 1) is no longer necessary and, therefore, is replaced by the aforementioned rigid connection of the fluid flow conduit to the chassis base. In addition, the first chassis part (17C) does not include a first catch part (item 3, FIG. 1), and the fluid flow conduit bore opening (14C) is openly presented at a terminal end of the fluid flow conduit (10C) which is permanently housed within the fluid flow sheath opening of the axially compressible sheath of the connector (100) and is permanently surrounded by the second bearing surface (4C) and the terminal end of the axially compressible sheath. This places the terminal end of the axially compressible sheath in permanent fluid communication with the fluid flow outlet port (7C).

The connector (100) includes the second chassis part (16C), such as is described above with reference to FIG. 1, and comprises a second catch part (5C) and a third bearing surface (6C), accordingly.

Figure 5:
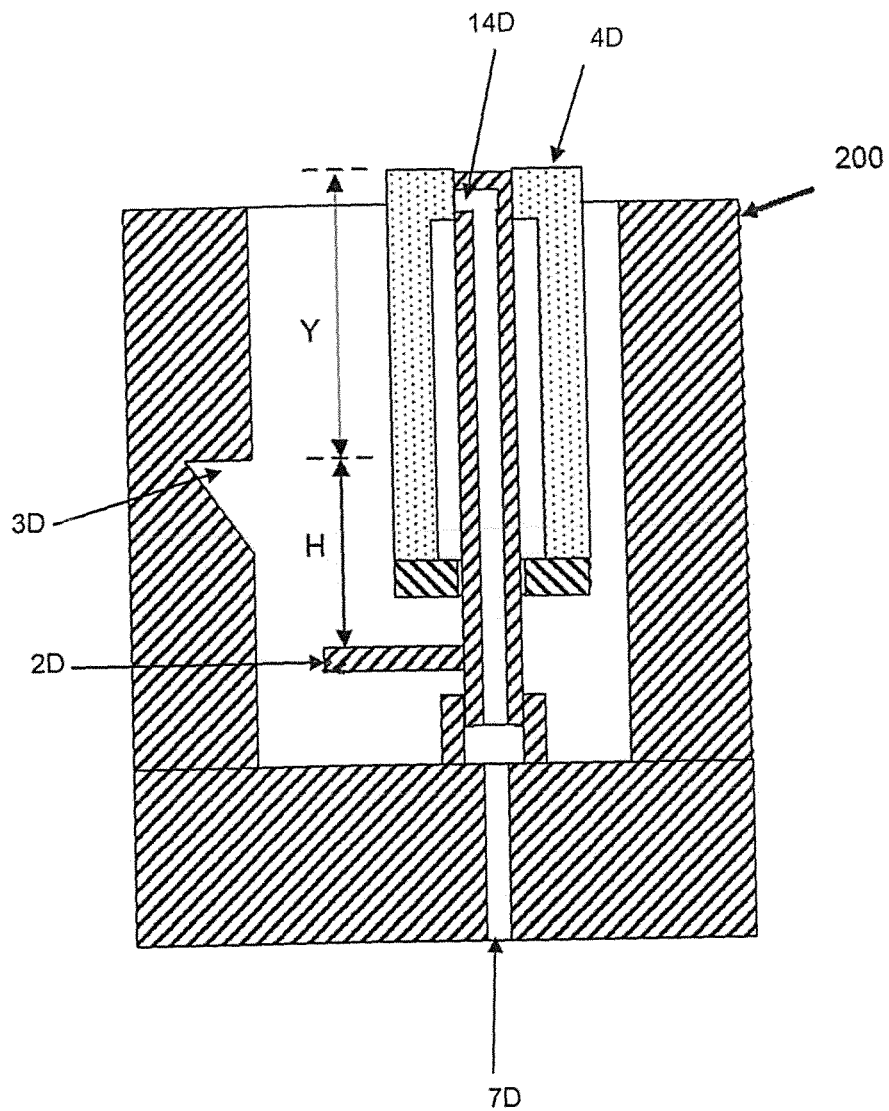
FIG. 5 shows a cross-sectional schematic view of a connector according to an embodiment of the invention, for connection with the connector of FIG. 4.

FIG. 5 schematically illustrates a cross-section view of a connector (200) according to an embodiment of the invention, which is similar to the connector described above in the environment referred to with reference to FIG. 1, except for the following differences. In particular, the connector of figure five comprises no second chassis part (item 16; FIG. 1), such as is described above with reference to FIG. 1, and comprises no second catch part (item 5; FIG. 1) nor third bearing surface (item 6; FIG. 1), accordingly. However, the connector (200) does include a first catch part (3D) which is configured to cooperate with the second catch part (5C) of the connector (100) illustrated in FIG. 4.

Figure 6A:
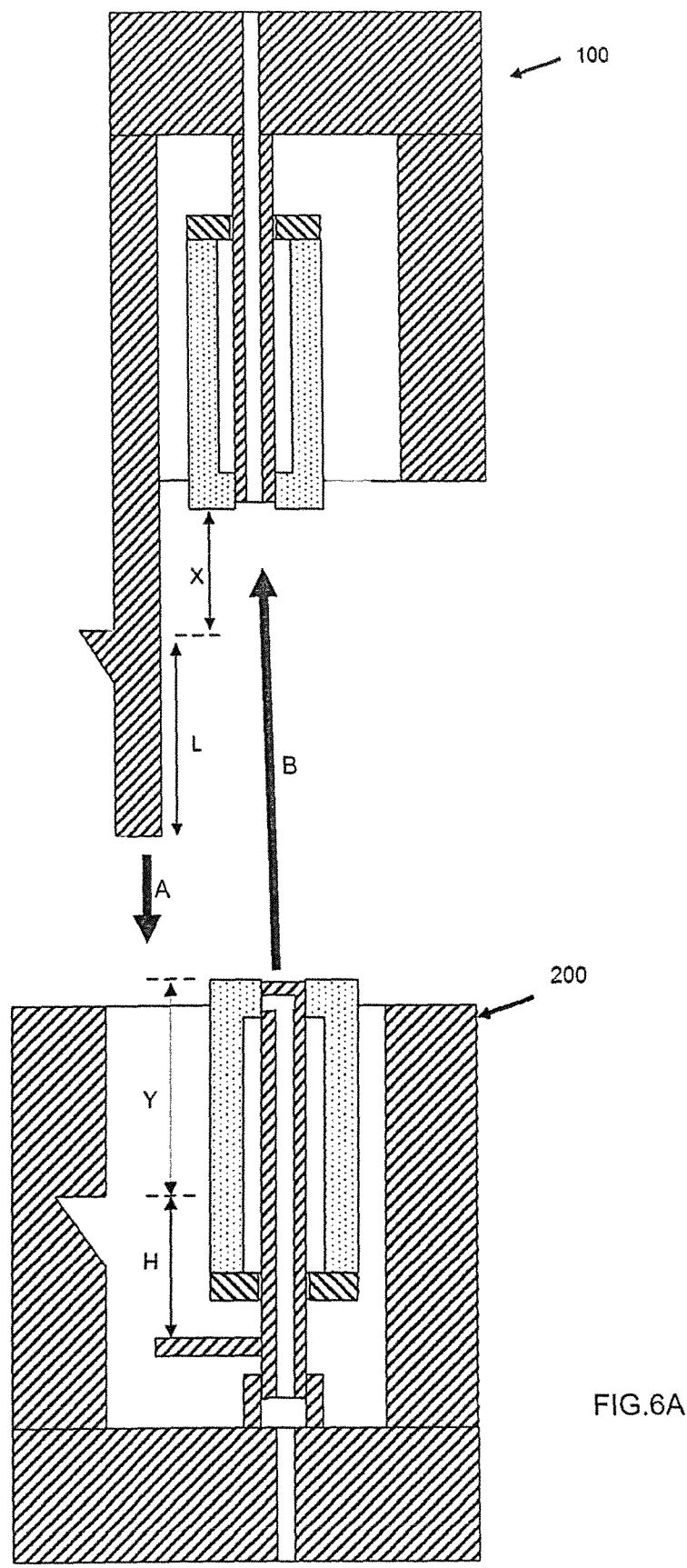
FIG. 6A shows a cross-sectional schematic view of a connector of FIG. 4 in the process of being connected with the connector of FIG. 5.

FIG. 6A schematically illustrates the manner in which the connector (100) of FIG. 4 is adapted to connect with the connector (200) illustrated in FIG. 5. In particular, an urging force (A) is directed via the third bearing surface (6C) of the "male" connector (100) against the first bearing member (2D) of the "female" connector (200) as the second catch part (5C) of the "male" connector approaches a position of engagement with the first catch part (3D) of the "female" connector (200). The second bearing surface (4D) of the "female" connector (200) urges against the second bearing surface (4C) of the "male" connector (100) with an urging force (B) to form a sealing interface surrounding the fluid flow conduit bore openings (14C, 14D) formed within the terminal ends of the fluid flow conduits of each of the two connectors in question. Simultaneously, the urging force (A) causes retraction of the fluid flow conduit of the "female" connector (200) to an extent sufficient to retract the fluid flow conduit bore opening (14D) from within the fluid flow sheath opening at the terminal end of the axially compressible fluid flow sheath to place the fluid flow conduit bore openings (14C, 14D) of the "male" and "female" connectors (100, 200) in fluid communication via a fluid-tight sealing interface formed by the second bearing surfaces (4C, 4D) that are pressed together.

Figure 6B:
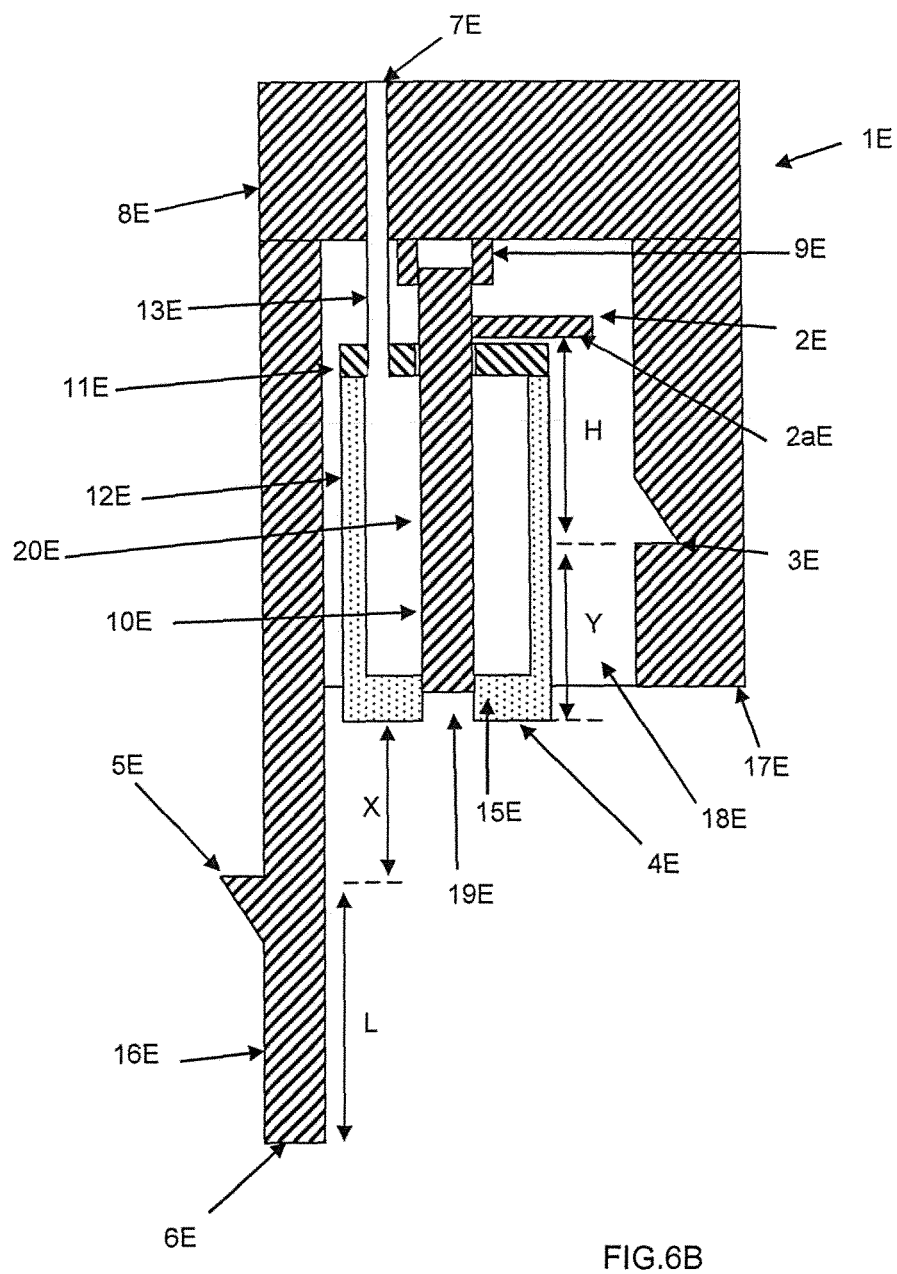
FIG. 6B shows a cross-sectional schematic view of a connector according to an embodiment of the invention.

FIG. 6B schematically illustrates a cross-sectional view of another embodiment of the invention in the form of a modified connector (1E) which is also consistent with the embodiment illustrated and described above with reference to FIG. 1, except for the following modifications. In particular, the fluid flow conduit (10) illustrated and described above with reference to FIG. 1, is replaced by a fluid flow blockage part (10E) of the modified connector which does not contain a fluid flow conduit bore. This is to be contrasted with the presence of a fluid flow conduit bore (item 13, FIG. 1) in other embodiments. In addition, a fluid flow conduit bore (13E) extends from the fixed sheath footing (11E) of the modified connector through the chassis cavity (18E) of the modified connector and terminating in fixed fluid communication with the fluid flow port (7E) of the modified connector, so as to place the sheath cavity (20E) of the modified connector in fluid communication with the fluid flow port thereof.

In this sense, it is to be understood that the fluid flow conduit (10) described above with reference to FIG. 1 serves the function of providing a retractable fluid flow blockage part sheathed within the axially compressible sheath part (12) in the same way that the fluid flow blockage part (10E) also serves the function of providing a fluid flow blockage part sheathed within an axially compressible sheath part (12E). Both retractable fluid flow blockage parts are retractable to enable fluid communication between a fluid flow sheath opening (19, 19E) and a fluid flow port (7, 7E) of the respective connector (1, 1E). In the case of the embodiment illustrated with reference to FIG. 1, the fluid flow conduit (10) also serves the additional function of providing a fluid flow passageway (13), whereas in the case of the embodiment illustrated with reference to FIG. 6B, the fluid flow conduit is provided by the sheath cavity (20E) and a separate fluid flow conduit bore (13E) collectively, which place the sheath cavity in fluid communication with the fluid flow port (7E) within the chassis base of the connector illustrated in FIG. 6B.

Otherwise, the remaining elements and components of the connector (1) described above with reference to FIG. 1 are also present as corresponding elements and components, with the same structure and function, in the modified connector (1E) described herein with reference to FIG. 6B. In particular, the modified connector comprises a chassis cavity (18E) defined by a chassis base (8E) and a first chassis part (17E) from which extends a second chassis part (16E) in the form of a limb or finger-like protrusion which presents a second catch part (5E) and a third bearing surface (6E). A first catch part (3E) is defined within an internal wall of the first chassis part within the chassis cavity. Within the chassis cavity is disposed an axially compressible sheath (12E) mounted one a fixed sheath footing (11E) through a through-opening of which passes a portion of the fluid flow blockage part (10E) that is not sheathed within the axially compressible sheath (12E) and which terminates within a bushing (9E) fixed to the chassis base (8E) within the chassis cavity. Also fixed to a side of the un-sheathed portion of the fluid flow blockage part is a first bearing member (2E) which presents a first bearing surface (2aE) accessible externally via the chassis cavity (18E). The sheathed portion of the fluid flow blockage part (10E) is retractable into the sheath cavity (20E) in response to the application of an urging force (as in force B shown in FIG. 3) against the first bearing surface (2aE) in the manner described above. Such retraction withdraws a terminal end of the fluid flow blockage part (10E) from within the fluid flow sheath opening (19E) formed in the terminal end of the axially compressible sheath (12E), and surrounded by the second bearing surface (4E) defined by the axially compressible sheath to form a sheath end seal (15E), and in doing so opens the fluid flow sheath opening (19E) permitting fluid communication with a fluid flow conduit bore (13E) which is in fluid communication with the sheath cavity (20E) via a through-opening formed in the fixed sheath footing (11E).

Figure 7:
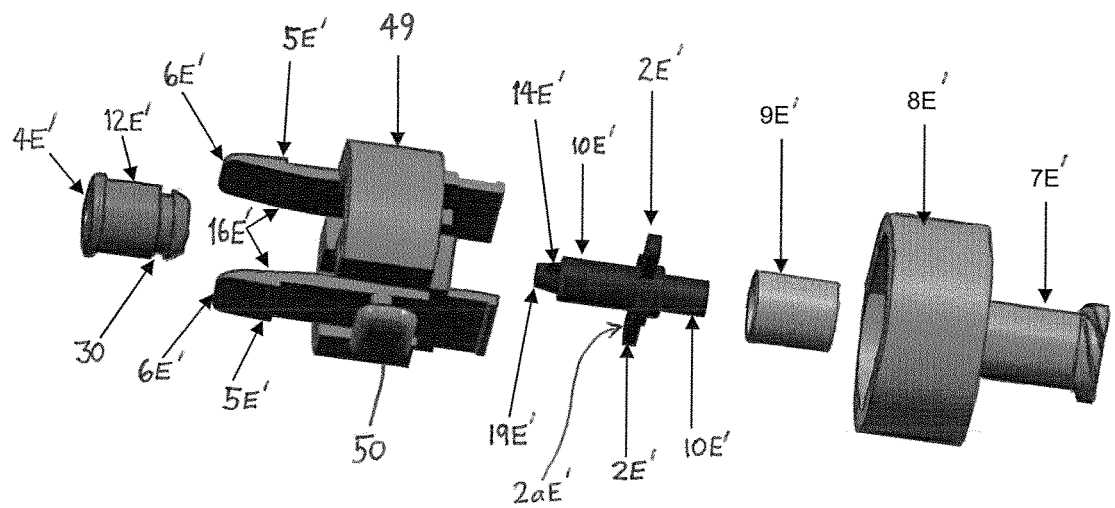
FIG. 7 and FIG. 8 show an exploded view and an exploded cross-sectional view, respectively, of a connector according to an embodiment of the invention.
Figure 8:
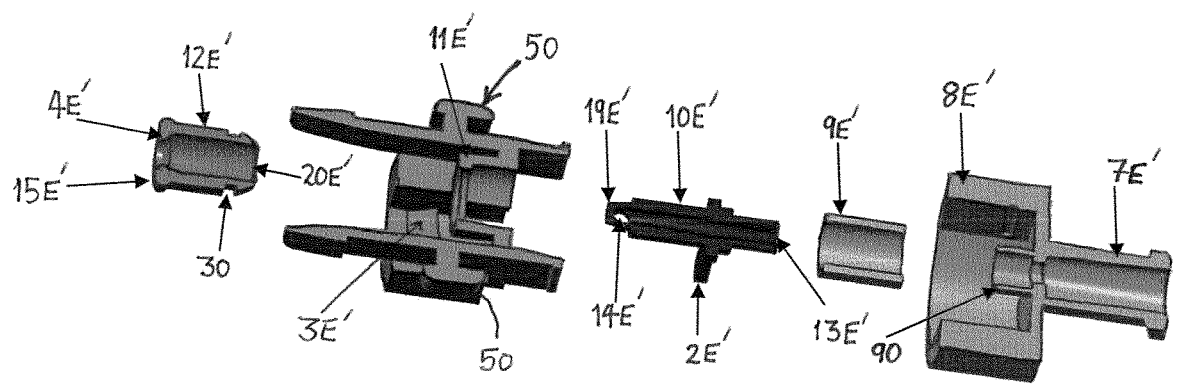

Referring to FIG. 7 and FIG. 8, there are shown an exploded view (FIG. 7) and a corresponding cross-sectional exploded view (FIG. 8), of another embodiment of the invention. The elements and components of the connector (1) described above with reference to FIG. 1 are also present as corresponding elements and components, with the same function, in the connector described herein with reference to FIG. 7 and FIG. 8. In particular, the connector comprises a chassis cavity defined by a chassis base (8E') from which extends a detachable second chassis part (49) which defines a pair of parallel and substantially identical opposed limb or finger-like protrusions (16E') which each outwardly present a respective second catch part (5E') and terminate at a respective third bearing surface (6E'). The second chassis part also defines a pair of opposed and substantially identical first catch parts (3E') each one of which is defined within an internal wall of a through-opening bore of the generally annular second chassis part. Within the through-opening bore is disposed an axially compressible sheath (12E') mounted upon a fixed sheath footing (11E') through a through-opening of which passes a portion of the fluid flow blockage part (10E') that is not sheathed within the axially compressible sheath (12E') and which terminates within a resiliently deformable, and axially compressible, bushing (9E') attached to the chassis base (8E') via a sealing interface fit against the outer surface of a coupling nozzle (90) protruding from the surface of the chassis base in fluid communication with a fluid flow port (7E') of the connector.

Also fixed to a side of the un-sheathed portion of the fluid flow blockage part is a first bearing member (2E') which presents a first bearing surface (2aE') accessible externally via the through-opening bore of the generally annular second chassis part (49). The sheathed portion of the fluid flow blockage part (10E') is retractable into the sheath cavity (20E') in response to the application of an urging force (such as force B, shown in FIG. 9) against the first bearing surface (2aE') in the manner described above. Such retraction withdraws a terminal end of the fluid flow blockage part (10E') from within the fluid flow sheath opening (19E') formed in the terminal end of the axially compressible sheath (12E'), and surrounded by the second bearing surface (4E') defined by the axially compressible sheath to form a sheath end seal (15E'), and in doing so opens the fluid flow sheath opening (19E') permitting fluid communication with a fluid flow conduit bore (13E') which is in fluid communication with the sheath cavity (20E') via a fluid flow conduit bore opening (14E'). In turn, fluid communication is achieved with the fluid flow port (7E') via the axially compressible bushing (9E') within which a terminal open end of the fluid flow conduit bore resides (i.e. the end which is opposite to the one containing the fluid flow conduit bore opening).

Reference is now made to FIG. 9, FIG. 10, FIG. 11, and FIG. 12, collectively, which show a cross-section view of a sequence of successive, reversible steps/positions for interconnecting two identical copies of the connector which are illustrated in FIG. 7 and FIG. 8 in exploded-view form, and which are illustrated in assembled form in FIGS. 9 to 12.

It is to be noted that the pair of parallel second chassis parts (16E') of each connector oppose each other in a first direction across the elongate axis of the fluid flow blockage part (10E'), and the connector as a whole. Similarly, the pair of first catch parts (3E') of each connector also oppose each other in a second direction across the elongate axis of the fluid flow blockage part (10E'), and the axially compressible sheath (12E'), and the connector as a whole. Notably, the first direction is substantially perpendicular to the second direction. This means that the pair of parallel second chassis parts (16E') of one of the two connectors does not obstruct the corresponding pair of parallel second chassis parts (16E') of the other one of the two connectors and, concurrently, each one of the pair of first catch parts (3E') of one of the two connectors is readily accessible by a respective one of the pair of second catch parts (5E') of the other one of the two connectors.

Figure 9:
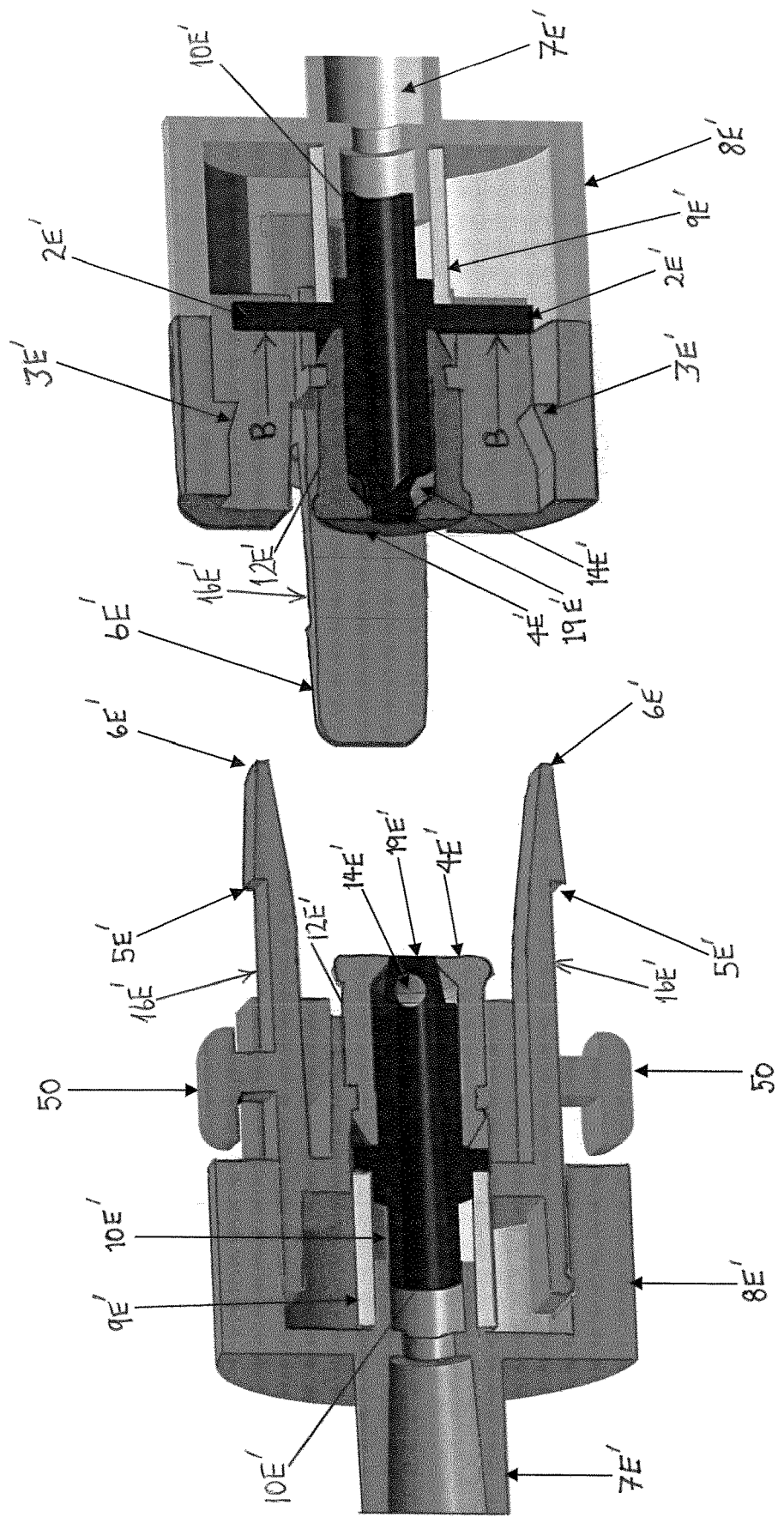
FIG. 9 shows a cross-sectional view of two connectors, each identical to each other, in the process of being connected (or disconnected) according to an embodiment of the invention.

FIG. 9 shows the two identical connectors fully separated, but coaxially aligned with the two second chassis parts (16E') of each one of the two connectors positioned in register with (but separated from) the first catch parts (3E') of each one of the other of the two connectors. Subsequent movement of the two connectors together, while maintaining this axial alignment allows connection to be formed as illustrated sequentially in FIG. 10, FIG. 11 and FIG. 12.

Figure 10:
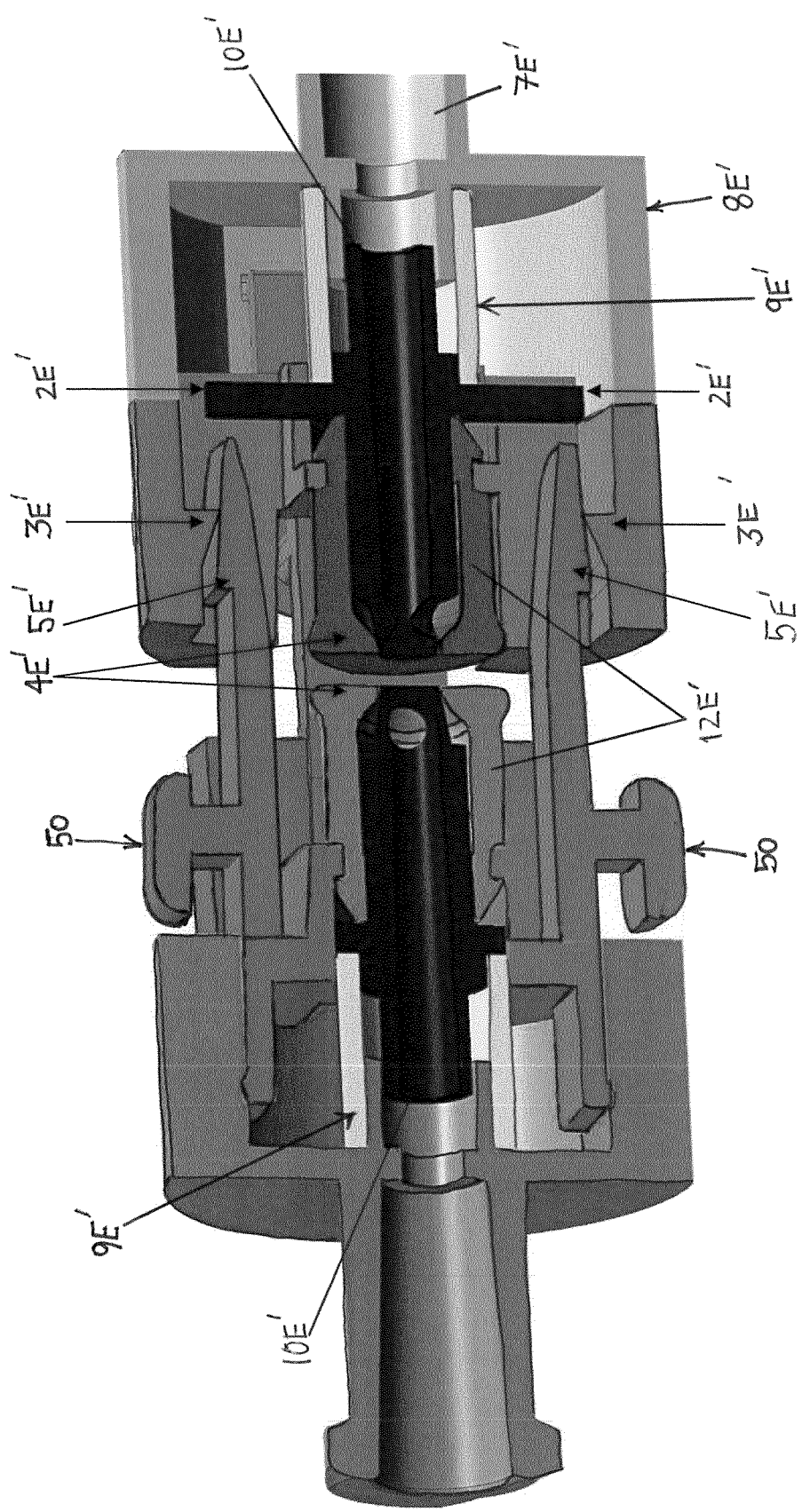
FIG. 10 shows a cross-sectional view of two connectors, each identical to each other, in the process of being connected (or disconnected) according to an embodiment of the invention.

In particular, FIG. 10 shows a relative positioning of the two connectors in which the two second chassis parts of each of the two connectors makes sliding contact with a first catch part of the other one of the two connectors, but before full connection is achieved. It is to be noted that the first catch part and the second catch part are not engaged in this position, and the second bearing surface (4E') of each one of the two connectors remains isolated from the second bearing surface of the other of the two connectors. Similarly, the third bearing surface of each of the second chassis parts of each connector remains isolated from the first bearing member (2E') of each of the two connectors.

Figure 11:
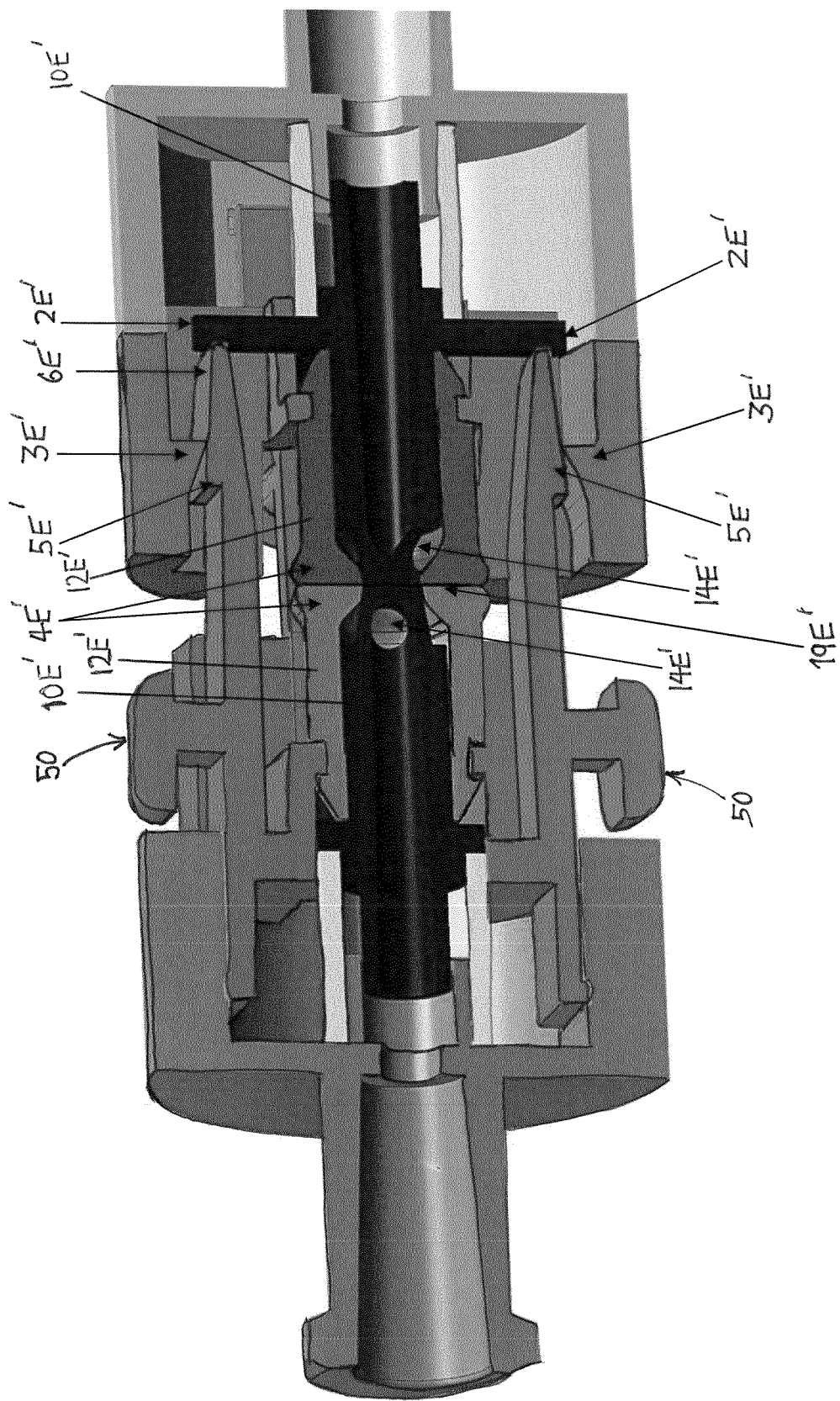
FIG. 11 shows a cross-sectional view of two connectors, each identical to each other, in the process of being connected (or disconnected) according to an embodiment of the invention.

FIG. 11 shows the relative positioning of the two connectors in which the third bearing surfaces of each one of the two connectors has just engaged with the first bearing surface upon the first bearing member of the other of the two connectors. At this point, retraction of the fluid flow blockage part (fluid flow conduit, 10E') is about to begin, and a compressive sealing interface has been formed by the second bearing surfaces (4E') of each of axially compressible sheaths (12E') of the two connectors to form a sealing interface around the fluid flow sheath opening (19E') at the end of each of the two abutting sheaths.

Figure 12:
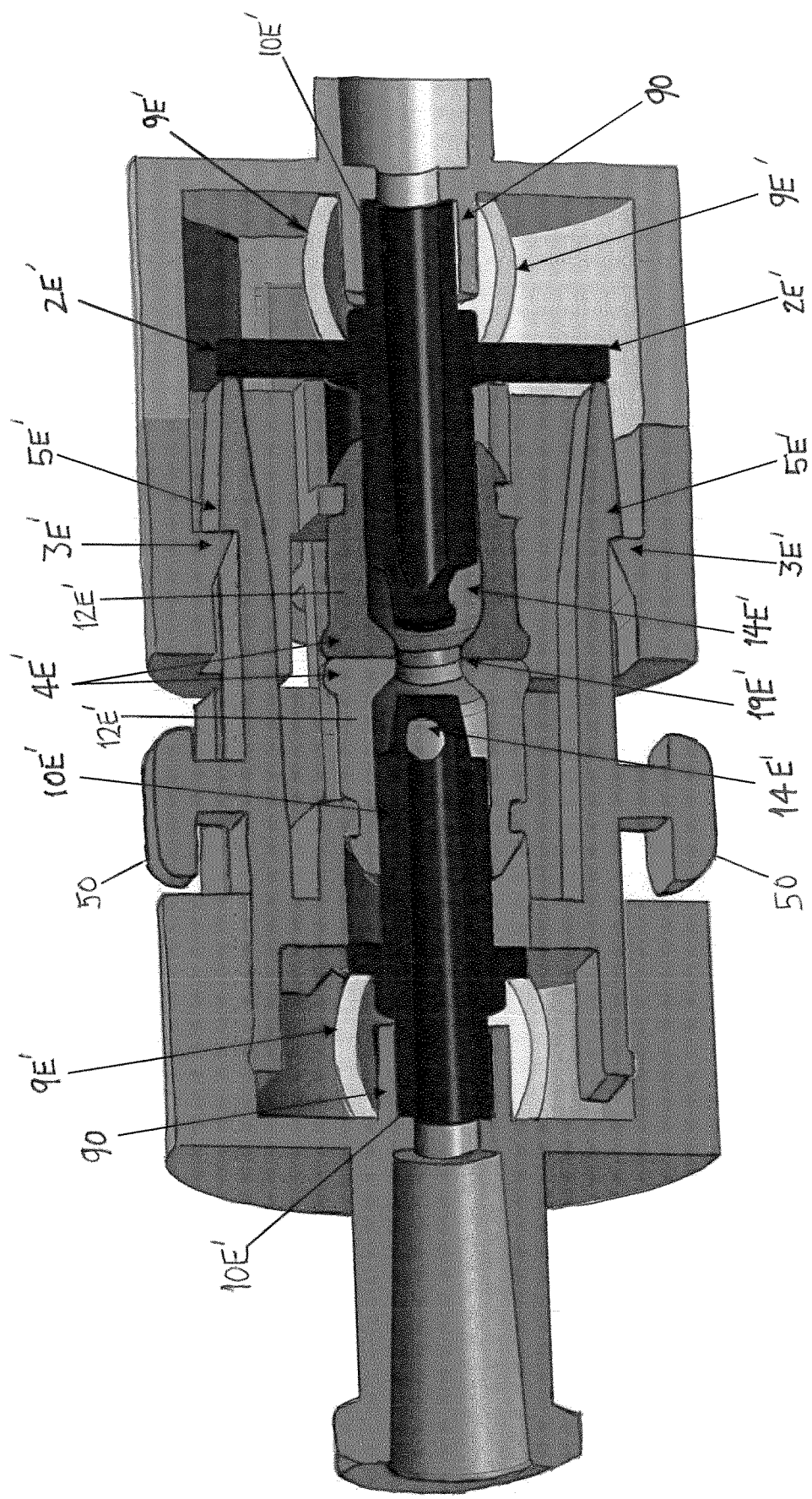
FIG. 12 shows a cross-sectional view of two connectors, each identical to each other, in the connected state according to an embodiment of the invention.

FIG. 12 shows the relative positioning of the two connectors in which axial advancement of the two connectors towards each other is progressed such that the third bearing surface of each one of the two connectors presses against the first bearing surface of each other one of the two connectors so as to retract the fluid flow blockage part (fluid flow conduit, 10E') axially within the respective axially compressible sheath containing the fluid flow blockage part in question. This occurs while the sealing interface around the fluid flow sheath opening (19E') at the end of each of the two abutting sheaths is maintained and enhanced by the aforementioned axial advancement of the two connectors.

It is noted that the axially compressible bushing (9E') within which a terminal open end of the fluid flow conduit bore resides of its connector resides, is abutted by the adjacent first bearing members of the connector within which it resides so as to be compressed by action of the aforementioned axial advancement. Each compressible bushing is formed of a resiliently deformable material which responds to the axial advancement by urging a reactive biasing force back against the first bearing member (2E') so as to balance the urging force which is applied to the first bearing member of one of the two connectors by the third bearing surface of the other one of the two connectors. The axial advancement, as shown in FIG. 12, is sufficient to cause the second catch part each of the two second chassis parts of each one of the two connectors to engage with the first catch part on each one of the other of the two connectors so as to connect the two connected together in a click-fit action.

Disengagement of the first and second catch parts is achieved by applying an inward radial force to the detachment buttons (50) formed on the outwardly-facing surface of the limb of each of the second chassis parts of the first and second connectors. Those limbs are resiliently deformable so as to respond to the inward radial force by flexing inwardly to move the second catch parts formed upon the limbs in question to slidingly separate, in an inward radial direction, from the first catch parts with which they are otherwise engaged. Subsequent axial retraction of the two connectors, whilst maintaining the inward radial force, allows simple disconnection of the two connectors.

Referring to FIGS. 13 to 18, there is shown there is shown a sequence of views of the connector according to a modification of the embodiment illustrated in FIGS. 7 to 12 in which there is further included an indexing mechanism configured for positioning a counter/counting piece by rotation through a predetermined interval of rotation so as to move a succession of different numerical symbols into, and subsequently out of, alignment with a display window for viewing by a user.

The first chassis part (8E') houses within it a cylindrical cam ring (52) which is rotatably housed within the chassis part such that the central cylindrical axis of the cylindrical cam ring coincides with the central longitudinal axis of the connector. The cylindrical cam ring is rotatable freely about the longitudinal axis of the connector. It is to be noted that, in FIGS. 13 to 18, a "transparent panel" (42) is presented in the side-wall of the first chassis part purely for the purposes of clarity and to aid a better understanding of the invention in this particular embodiment. However, it is important to note that the "transparent panel" (42) is not present within the actual product illustrated in these figures. The benefit of the "transparent panel" is that it permits visualisation of the cylindrical cam ring (52) within the chassis part, and the cam follower (46) in relation to a pair of opposed cams (44, 45) formed within the cylindrical wall of the cylindrical cam ring, and this visualisation greatly assists in explaining the operation of these components.

However, a viewing window (40) is genuinely formed within the side wall of the first chassis part in order to permit the presentation of numerical counting symbols (41) which are formed upon an outer, convex cylindrical surface of the cylindrical cam ring (52). The purpose of the viewing window is to permit single counting symbols, in succession from amongst a plurality of different individual counting symbols, to be presented through the window so as to be visible on the side of the first chassis part, in use. The radius of curvature of the outer convex cylindrical surface of the cylindrical cam ring is slightly less than the radius of curvature of the inner concave cylindrical surface of the first chassis part (8E') within which it resides, with the outer convex cylindrical surface of the former positioned in direct opposition to the concave inner cylindrical surface of the latter, such that the former is able to slide across the latter by rotation of the former around the longitudinal cylindrical axis of the latter. This rotation is urged by the longitudinal axial movement of the cam follower (46) back-and-forth along the longitudinal axis of the first chassis part which urges the cam follower, in succession, against the cam surfaces of the pair of opposed cams (44, 45).

Each of the cams (44,45) comprises a sawtooth surface defining one of the two opposing edges of a respective one of two semi-circumferential zigzag channels cut into the inner, concave surface of the cylindrical cam ring (52). At the terminal end of each of the two first bearing members (2E') projects a respective cam follower (46) in the form of a cylindrical lug disposed within a respective one of the two zigzag channels, being configured and disposed to be slidable along the respective channel between the opposing cam surfaces of the pair of opposed cams (44, 45) defined by the channel. It is to be noted that, in other embodiments, the respective cam followers may be other than cylindrical. For example, the cam followers may each comprise an ellipsoidal or semi-circular shape. This shaping may reduce the potential jamming of the system and allows for more manufacturing tolerance at smaller sizes. The opposed cams comprise a first undulating cam surface (44) opposed by a second undulating cam surface (45). These cam surfaces are configured such that the "teeth" or peaks of one undulating cam surface coincided with the troughs of the opposing cam surface.

The cylindrical cam ring is restrained within the first chassis part such that axial movement of the cylindrical cam ring in a direction along the longitudinal axis of the first chassis part (and the axis of the connector as a whole) is prevented by the presence of retaining surfaces of the connector (e.g. flange, lug, abutment or bearing surface adjacent/against opposite cylindrical ends of the cam ring: not shown) configured and positioned to obstruct such longitudinal movement.

Figure 13:
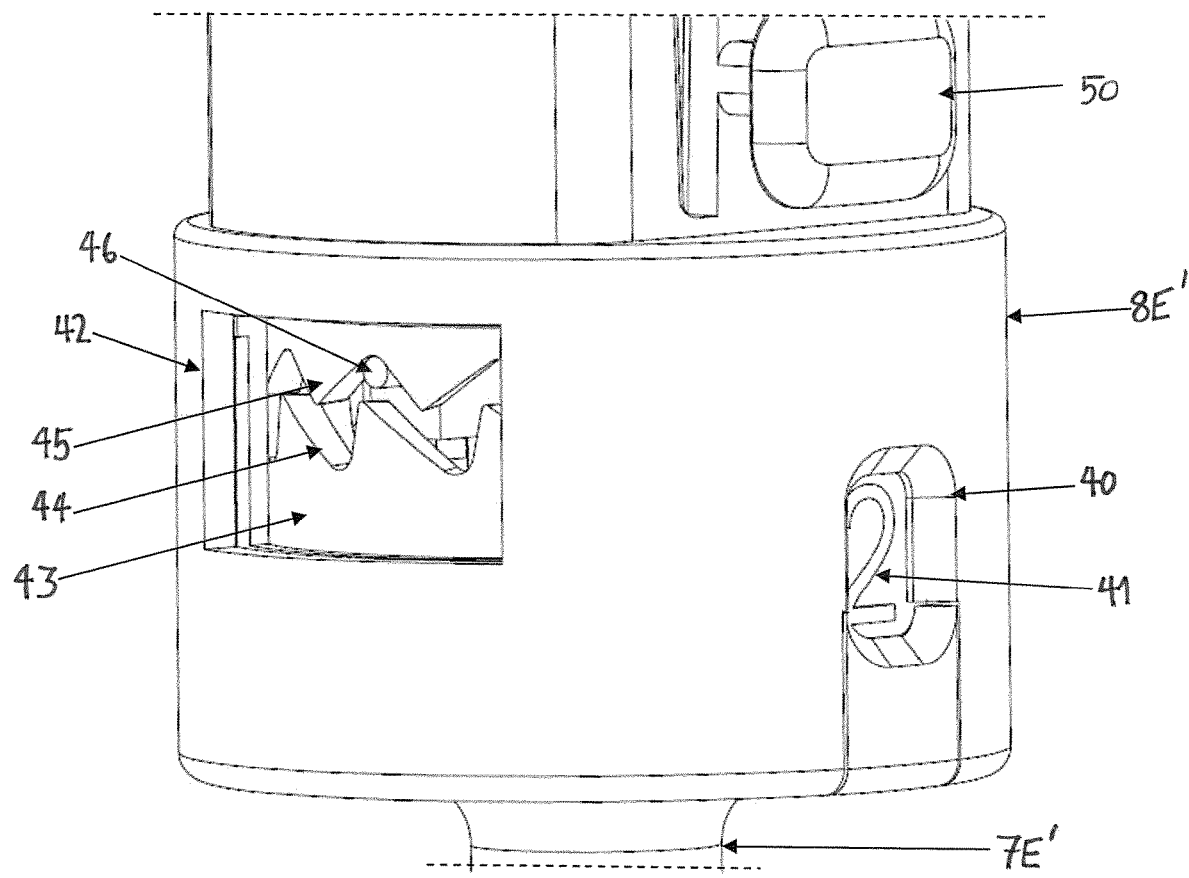
FIG. 13 to FIG. 18 show individual views of a part of a connector according to FIG. 9, including an indexing mechanism in successive stages along a process of operation according to an embodiment of the invention.

Referring to FIG. 13, the connector of which the first chassis part (8E') forms a part, is unconnected to another such connector such that the fluid flow blockage part (10E') is in the un-retracted state such as is illustrated in FIG. 9. In this state, the resiliently deformable bushing (9E') maintains the first bearing members (2E') of the fluid flow blockage part separated from the fluid flow port (7E') first chassis part to the maximum extent. In a condition illustrated in FIG. 13, each cam follower (46) is urged against the trough of the second cam (45) and does not engage the first cam (44). This condition positions the numerical symbol (41), shown as "2" in FIG. 13, at the viewing window (40) for viewing by a user.

FIG. 14, FIG. 15, FIG. 16 and FIG. 17 show a succession of positions of the cam follower relative to the first and second cams as the connector is connected to another such connector (FIG. 14 and FIG. 15), in the manner described above, and as the connector is subsequently disconnected from that of the connector (FIG. 16 and FIG. 17), in the manner described above.

Figure 14:
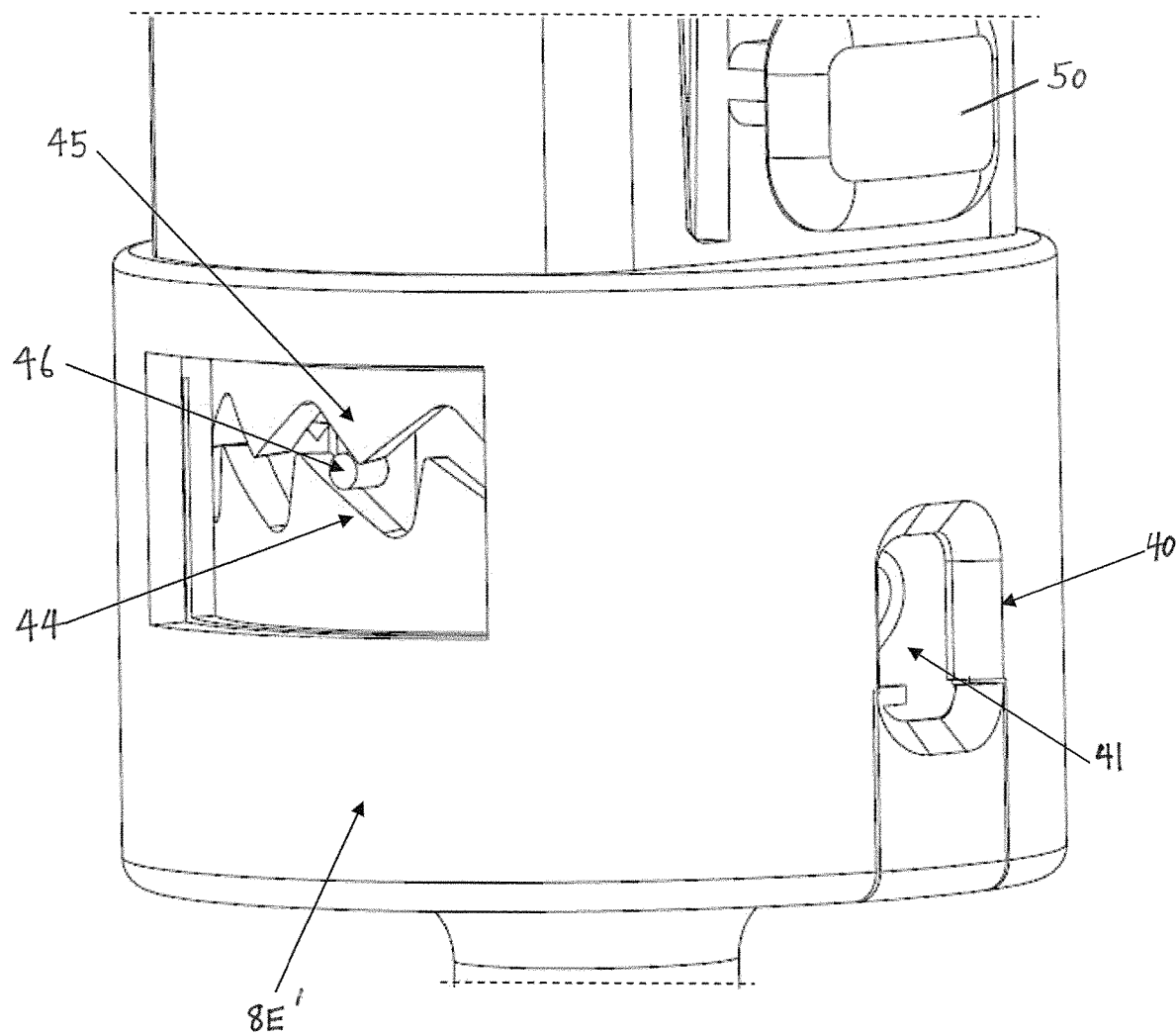
Figure 15:
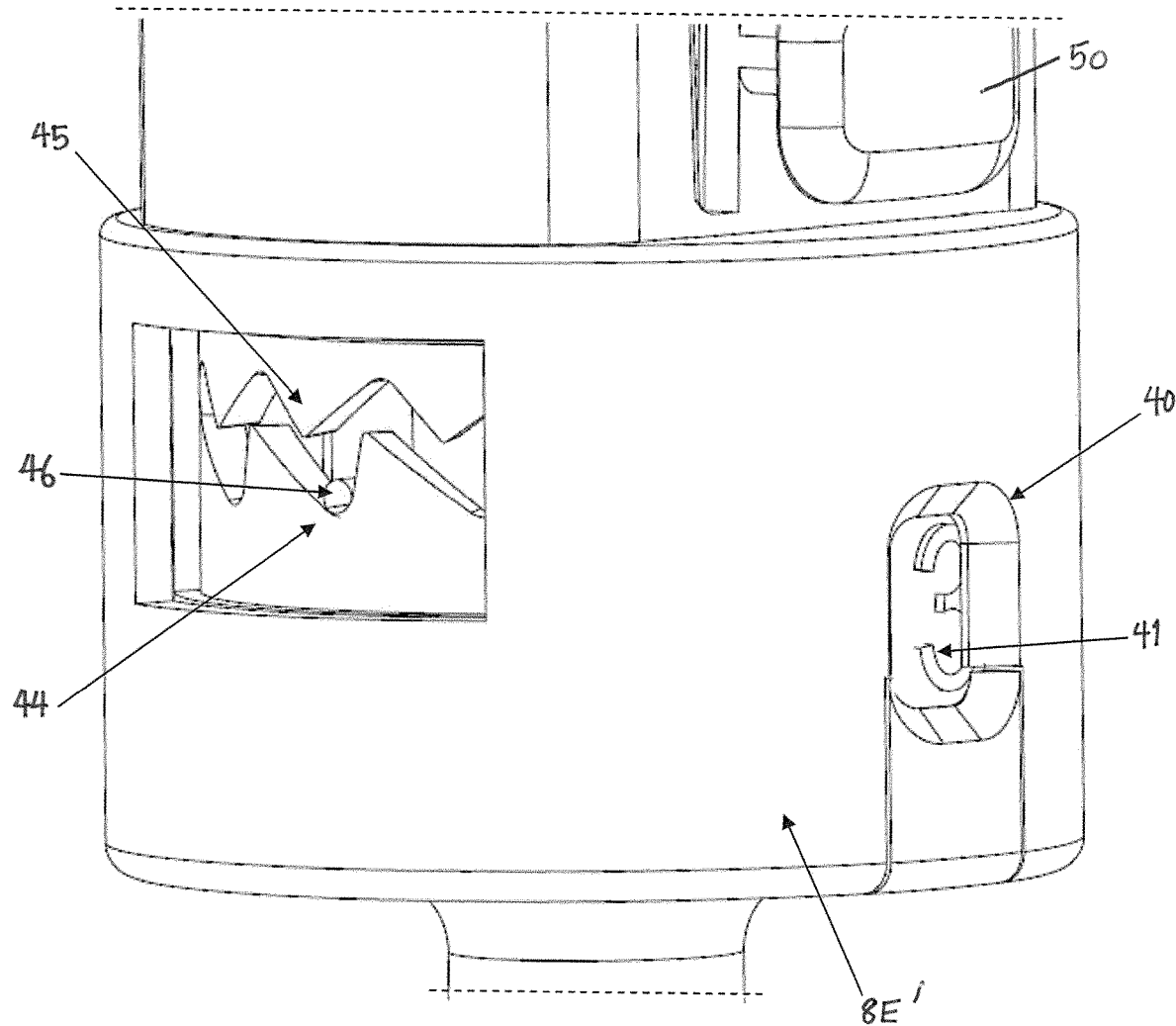

Referring to FIG. 14 and FIG. 15, connection of the connector to another such connector, as described above, causes retraction of the fluid flow blockage part (10E') and axial movement of the cam followers (46) against the inclined surface of the first cam (44), as shown in FIG. 14, and into the trough of the first cam, as shown in FIG. 15, so as to push the cylindrical cam ring to rotate around its cylindrical axis to move the numerical symbol "2" (41) out of alignment with the viewing window (40) and to bring a subsequent numerical symbol "3" (41) partially into alignment with the viewing window. In this condition, the cam follower (46) is retained in the trough of the first cam (44) while the two connectors are held connected together, as described above.

Figure 16:
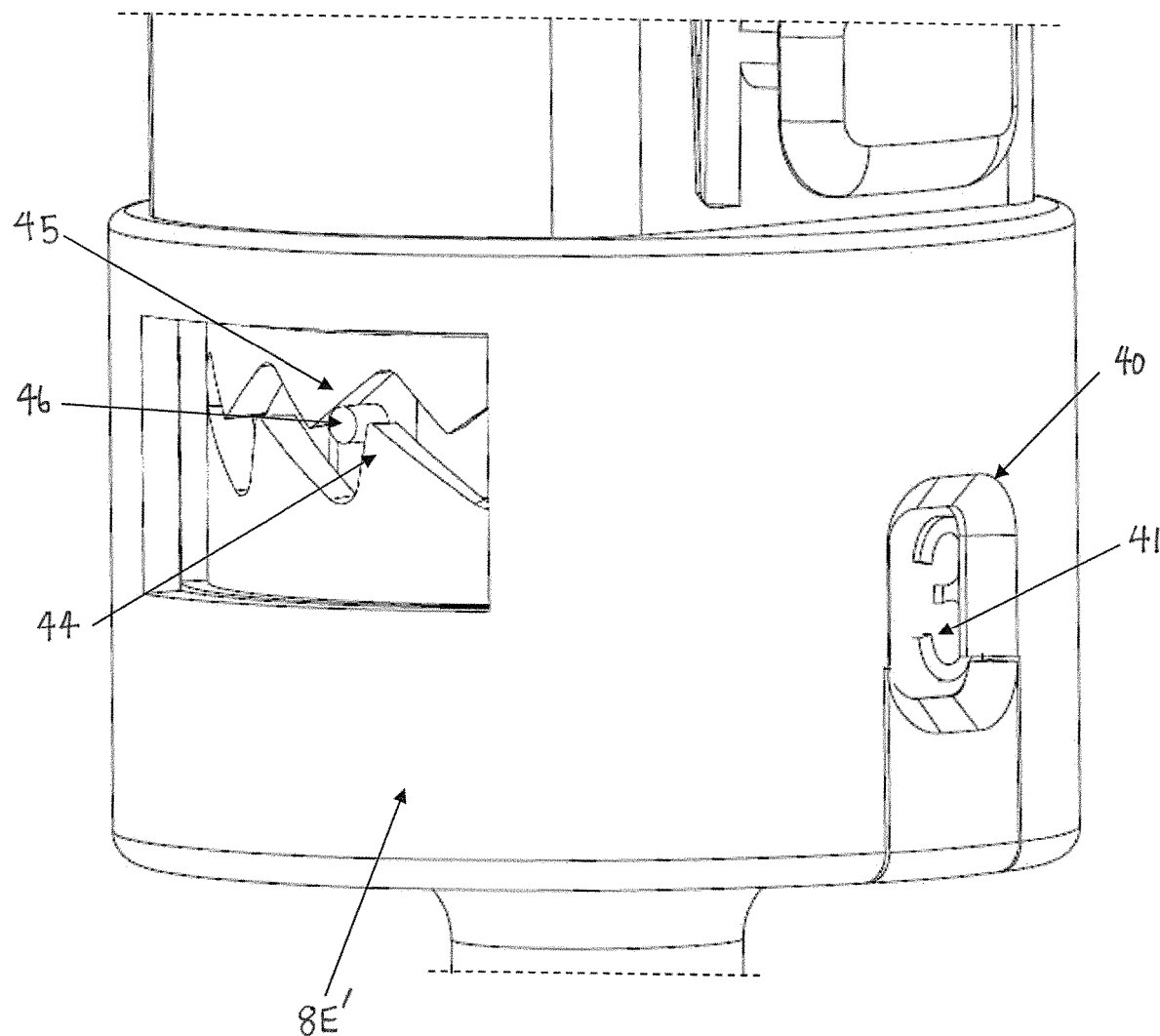
Figure 17:
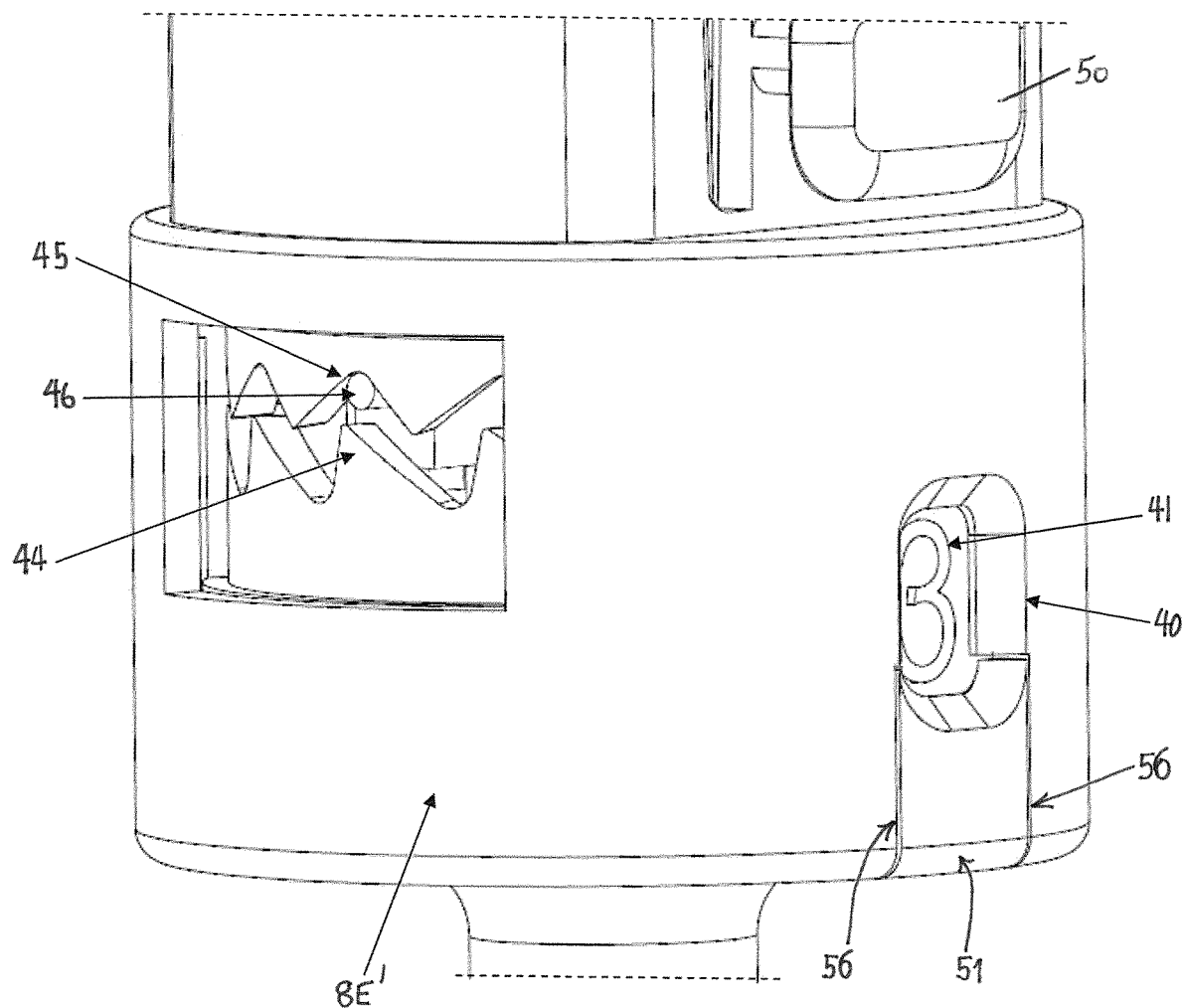

Subsequent disconnection of the two connectors causes the resiliently deformable bushing (9E') to urge the cam follower (46) away from the first cam (44) and against the second cam (45). The effect of this urging of the cam follower against the first is to cause the cylindrical cam ring to rotate about its cylindrical axis as the cam follower slides against the inclined cam surface of the second cam (45) towards the trough formation of the second cam as shown in FIG. 16 such that, ultimately, the cam follower resides within the trough of the second cam, as shown in FIG. 17, where it is urged to stay by the ageing force exerted by the resiliently deformable bushing. The effect of this additional rotation of the cylindrical cam ring is to move the subsequent numerical symbol "3" (41) fully into alignment with the viewing window (40). The result is that prior to the act of connecting the connector to another such connector, the numerical symbol "2" was fully aligned for viewing through the viewing window (40) of the connector indicating that the connector had been previously connected to another such connector two times previously, whereas the act of making a third such connection between connectors causes the numerical symbol "3" to be fully aligned for viewing through the viewing window (40) thereby indicating that the connector has now been previously connected to another such connector three times.

Each time such a connection is made, the cylindrical cam ring advances in rotation by an amount sufficient to bring a successive numerical symbol (41) into alignment for viewing through the viewing window (40) thereby allowing a user to immediately determine how many times the connector has been used to form such a connection.

Figure 18:
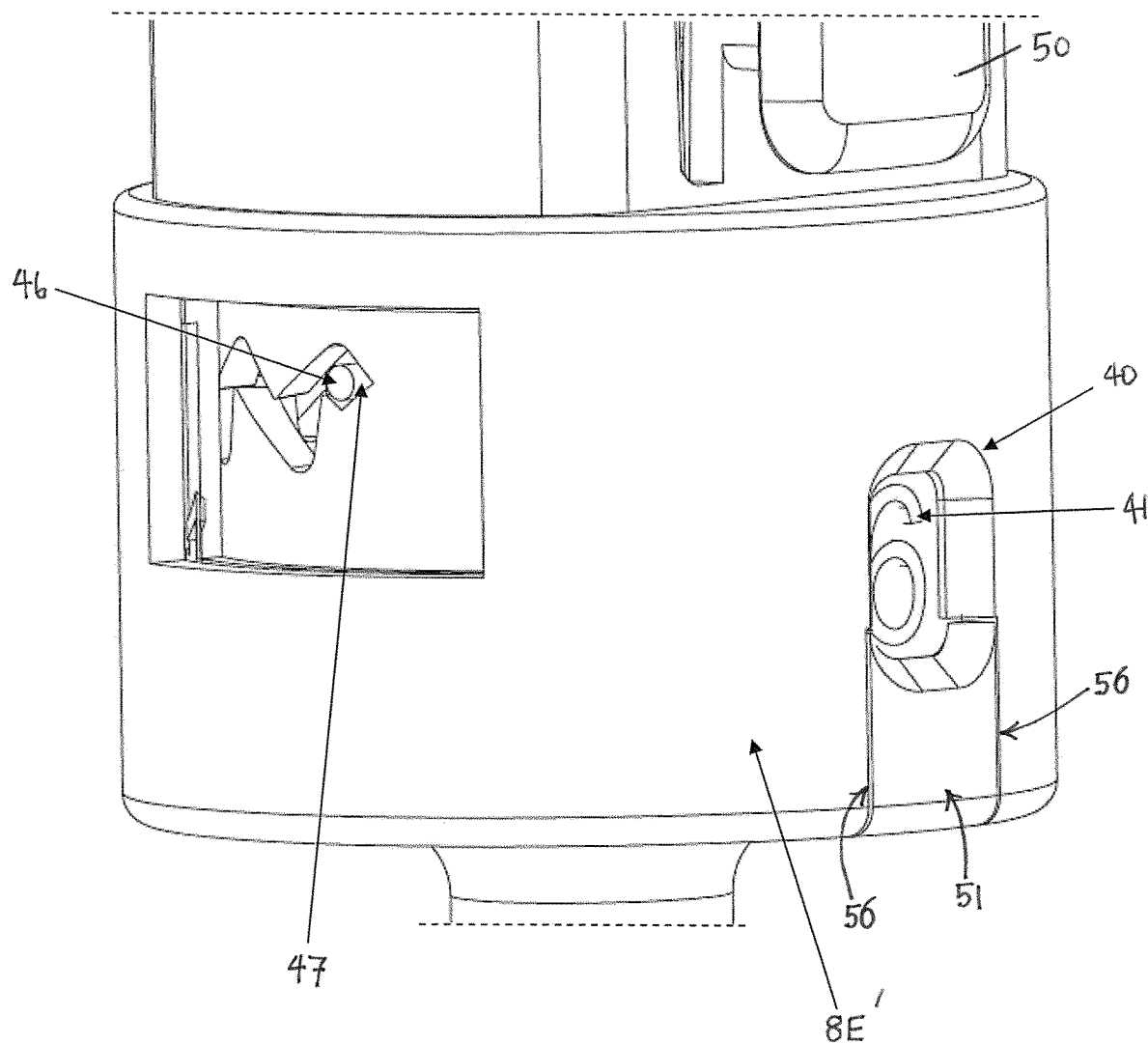
Figure 19:
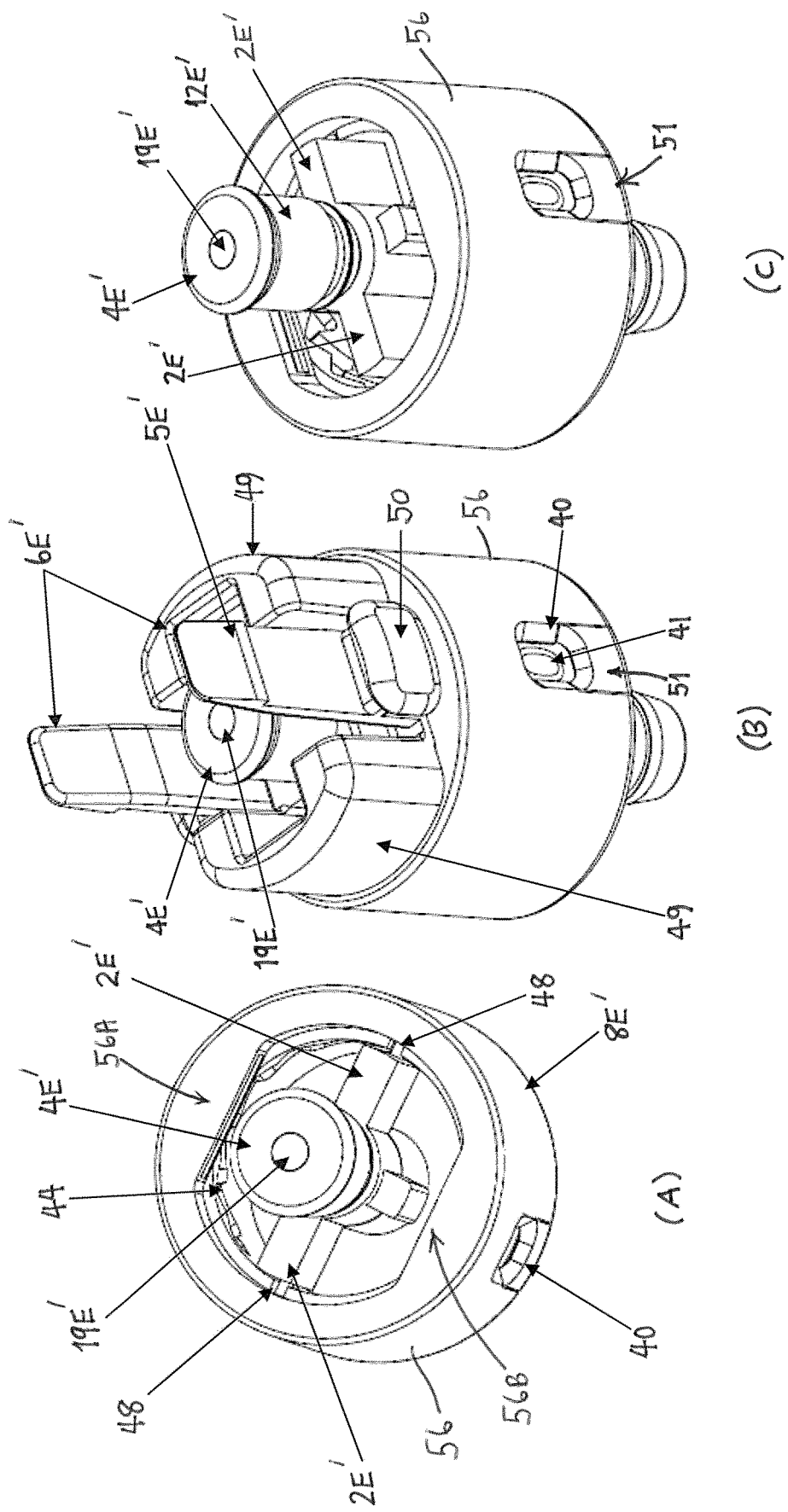
FIGS. 19(A), 19(B) and 19(C) show views of a part of a connector shown in FIGS. 9 to 12, including the indexing mechanism of FIGS. 13 to 18.
Figure 20:
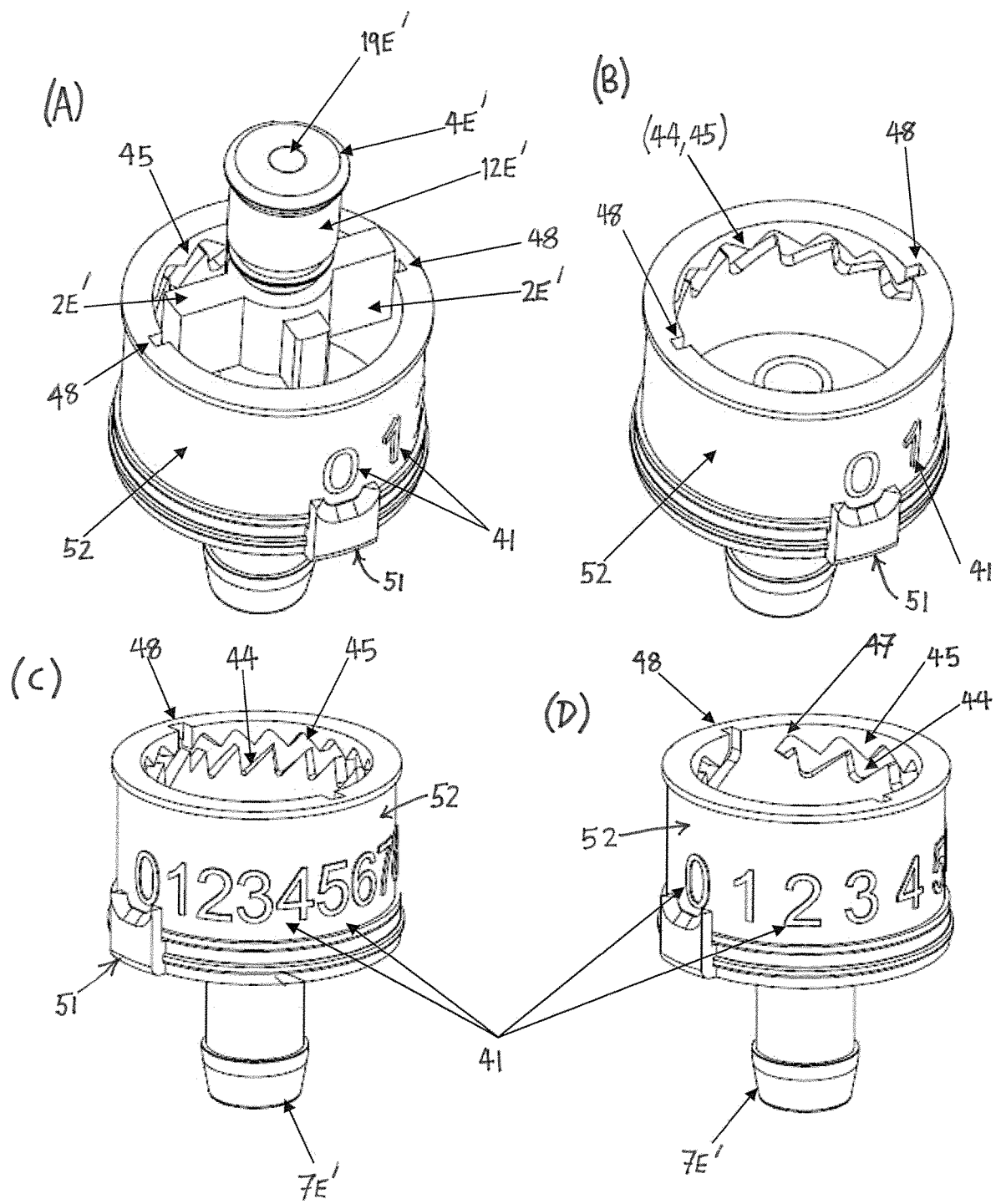
FIGS. 20(A), 20(B), 20(C) and 20(D) show views of parts of the indexing mechanism within the connector, or connector parts, shown in FIGS. 9 to 19(C), including the indexing mechanism of FIGS. 13 to 18.

Referring to FIG. 18, the respective ends of the semi-circumferential zigzag channel defining the first and second cams (44, 45) terminate at a respective terminal notch (47) configured to receive and retain a respective one of the two cam followers (46) to prevent further rotation of the cylindrical cam ring (52). This also prevents any further axial movement of the cam follower (46) and further movement of the first bearing members (2E'), therefore retaining the fluid flow blockage part (10E') in the fully un-retracted state preventing fluid flow through the connector. In this condition, the final numerical symbol of the sequence of numerical symbols (41), in this case, symbol "6", is aligned in register with the viewing window (40). The terminal notch ensures that the connector cannot subsequently be connected to another such connector, in this instance, on more than six occasions. This may be particularly important for safety reasons whereby the connector is deemed to require servicing, cleaning or may be considered to be unfit for further use after this number of uses. In this way, the connector is automatically rendered "safe". Conversely, at the opposite end of each semi-circumferential zigzag channel is formed and access slot (see FIGS. 19 and 20; item 48) by which a respective cam follower (46) may be inserted into the zigzag channel in question thereby to connect the first bearing members (2E') to the cylindrical cam ring.

The first cam (44) and against the second cam (45) collectively define a cam slot configured such that the cam follower can move only in one circumferential direction along the cam slot towards the terminal notch (47). This ensures that the indexing mechanism may count only in one order (ascent or descent) through the counting (e.g. numerical) symbols. The cam slot comprises two opposing arrays of successive cam peaks and troughs, with the first cam (44) defining one array and the second cam (45) defining the opposing array. Each peak of one array opposes a respective trough between two neighbouring successive peaks of the opposing array. Each such peak is circumferentially offset from the respective trough it opposes to bias the circumferential direction of movement of the cam follower along the cam slot towards the terminal notch (47). In particular, amongst a given of opposing trough and peak pairing, the trough of the pairing is circumferentially closer to the terminal notch than is the peak of that pairing.

FIG. 19A, FIG. 19B and FIG. 19C, together with FIG. 20A, FIG. 20B, FIG. 20C and FIG. 20D, show different views of component parts of the connector illustrated in FIGS. 13 to 18 in various states of assembly and orientation. In particular, the first chassis part (8E') comprises a two-part assembly including a base portion in which the fluid flow port (7E') is formed to project from a base plate portion upon a peripheral edge of which projects and alignment plug (51). The cylindrical cam ring (52) is dimensioned and configured to sit upon the surface of the base plate and to be rotatable relative to the base plate and the alignment plug. A second part of the two-part assembly includes a sleeve portion (56) defining a sleeve bore configured and arranged for receiving and retaining the cylindrical cam ring.

The peripheral edge of the sleeve portion (56) defines the periphery of the sleeve bore, and this is configured to meet the peripheral edges of the base plate portion such that the two peripheral edges meet in register and in alignment to retain the cylindrical cam ring (52) within the sleeve bore. The peripheral edge of the sleeve portion includes a slot dimensioned to receive, in a snug fit, the alignment plug (51) thereby to prevent rotation of the sleeve relative to the base plate portion and to simultaneously define the viewing window (40) by those portions of the slot which are not occupied by the received alignment plug and, thereby, define a through-opening or "window" in the first chassis part (8E').

Two retaining flanges (56A, 56B) extend partially over the sleeve bore at diametrically opposite sides of the upper end of the sleeve bore through which the fluid flow blockage part (10E') and the surrounding axially compressible sheath (12E') extend. These two retaining flanges obstruct axial movement of the cylindrical cam ring within the sleeve bore.

The invention claimed is:

1. A connector adapted for forming a fluid flow pathway therethrough by connection with a reciprocal connector, wherein both the connector and the reciprocal connector each comprise:
a fluid flow blockage part sheathed within an axially compressible sheath part and comprising a first bearing surface configured for receiving an urging force to push the fluid flow blockage part to retract axially along the sheath part and a terminal end of the sheath part defines a second bearing surface containing a fluid flow opening with the fluid flow blockage part retractably therein;
a first chassis part comprising a first catch part;
a second chassis part comprising a second catch part and a third bearing surface spaced from the second catch part along the second chassis part;
wherein the axial distance (Y) between the second bearing surface and the first catch part exceeds the axial distance (X) between the second bearing surface and the second catch part, and the axial distance (L) between the third bearing surface and the second catch part exceeds the axial distance (H) between the first bearing surface and the first catch part;
whereby the connector is connectable to the reciprocal connector with respective fluid flow openings mutually aligned such that $X+L \geq H+Y$ whereby said retraction takes place not before said mutually aligned respective fluid flow openings meet to form a fluid flow pathway between the sheath part of the connector and the sheath part of the reciprocal connector.

2. A connector according to claim 1 wherein the fluid flow blockage part comprises a fluid flow conduit part including a fluid flow conduit opening configured to enter into fluid communication with said sheath part when said retraction takes place, thereby to form a part of said fluid flow pathway.

3. A connector according to claim 1 wherein before the second catch part of the connector engages the first catch part of the reciprocal connector:
the sheath part of the connector and the sheath part of the reciprocal connector are reciprocally compressed at respective second bearing surfaces thereat to form a compression interface surrounding said respective fluid flow openings, whereby said retraction takes place not before said compression interface is formed.

4. A connector according to claim 3 wherein before the second catch part of the connector engages the first catch part of the reciprocal connector:

the fluid flow conduit part of the connector is retracted axially by said urging force applied at the first bearing surface thereof by said third bearing surface of the reciprocal connector, and the fluid flow conduit part of the reciprocal connector is retracted axially by said urging force applied at the first bearing surface thereof by said third bearing surface of the connector, whereby said retraction takes place not before said compression interface is formed.

5. A connector according to claim 1 in which said compression interface surrounding said respective fluid flow openings forms a sealing interface fully surrounding the respective fluid flow openings securing fluid communication therebetween.

6. A connector according to claim 1 in which said axial retraction of said fluid flow conduit part moves that fluid flow conduit part along said sheath part from a closed state of fluid isolation from said fluid flow opening thereof, to an open state of fluid communication with the fluid flow opening thereof.

7. A connector according to claim 6 in which a surface of the sheath part is shaped to abut a conduit opening of the fluid flow conduit part when in said closed state, and to be spaced from the conduit opening of the fluid flow conduit part when in said open state.

8. A connector according to claim 1 in which the sheath part is resiliently deformable.

9. A connector according to claim 1 in which the second chassis part comprises a resilient biasing member upon which the second catch part is disposed, wherein the connector is connectable to the reciprocal connector to flex the resilient biasing member to urge the second catch part of the connector towards the first catch part of the reciprocal connector.

10. A connector according to claim 1 in which one of the first catch part and the second catch part comprises a notch, depression or lip and the other of the first catch part and the second catch part comprises a detent configured to be received and retained by the notch, depression or lip.

11. A connector according to claim 10 in which the first catch part comprises the notch, depression or lip and the second catch part comprises the detent.

12. A connector according to claim 1 comprising an indexer configured to position a counter piece by rotation through a predefined interval of rotation.

13. A connector according to claim 12 in which the indexer comprises a cylindrical cam and a reciprocating cam follower, wherein the cam follower is connected to the fluid flow conduit part and is engaged within a cam slot of the cylindrical cam such that said axial retraction of the fluid flow conduit part causes the cam follower to urge rotation of the cylindrical cam around the axis of the fluid flow conduit part.

14. A pair of connectors in which each connector of the pair of connectors comprises a connector according to claim 1 whereby one connector of said pair of connectors is said reciprocal connector.

15. A connector system comprising a first connector and a second connector, wherein both the first connector and the second connector are adapted to connect to each other, wherein:
the first connector and the second connector each comprises a respective fluid flow blockage part sheathed within an axially compressible respective sheath part;
a terminal end of each respective sheath part defines a terminal bearing surface containing a fluid flow opening with the fluid flow blockage part retractably therein;
the first connector comprises a first chassis part comprising a first catch part and a first bearing surface spaced from the first catch part along the first chassis part;
the second connector comprises a second catch part and a second bearing surface configured for receiving an urging force to push the fluid flow blockage part of the second connector to retract axially along the respective sheath part;
wherein the axial distance (Y) between the second catch part and the terminal bearing surface of the second connector exceeds the axial distance (X) between the terminal bearing surface of the first connector and the first catch part, and the axial distance (L) between the first bearing surface and the first catch part exceeds the axial distance (H) between the second bearing surface and the second catch part;
whereby the first connector is connectable to the second connector with respective fluid flow openings mutually aligned such that before the first catch part of the first connector engages the second catch part of the second connector:
wherein X+L>H+Y whereby said retraction takes place not before said mutually aligned respective fluid flow openings meet to form a fluid flow pathway between the sheath part of the first connector and the sheath part of the second connector.

16. A connector system according to claim 15 wherein the fluid flow blockage part comprises a fluid flow conduit part including a fluid flow conduit opening configured to enter into fluid communication with said sheath part when said retraction takes place, thereby to form a part of said fluid flow pathway.

17. A connector system according to claim 15 wherein the first connector is connectable to the second connector such that the sheath part of the first connector and the sheath part of the second connector are reciprocally compressed at respective terminal bearing surfaces thereat to form a compression interface surrounding said respective fluid flow openings, whereby said retraction takes place not before said compression interface is formed.

18. A connector system according to claim 17 wherein the first connector is connectable to the second connector such that the fluid flow conduit part of the second connector is retracted axially by said urging force applied at the second bearing surface by said first bearing surface whereby said retraction takes place not before said compression interface is formed.

19. A connector system according to claim 17 in which said compression interface surrounding said respective fluid flow openings forms a sealing interface fully surrounding the respective fluid flow openings securing fluid communication therebetween.

20. A connector system according to claim 15 in which said axial retraction of said fluid flow conduit part moves that fluid flow conduit part along said sheath part from a closed state of fluid isolation from said fluid flow opening thereof, to an open state of fluid communication with the fluid flow opening thereof.

* * * * *